United States Patent
Padala

(10) Patent No.: US 9,510,948 B2
(45) Date of Patent: Dec. 6, 2016

(54) SYSTEMS, DEVICES AND METHODS FOR REPAIR OF HEART VALVE LESIONS

(75) Inventor: Saimuralidhar Padala, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/343,183

(22) PCT Filed: Sep. 7, 2012

(86) PCT No.: PCT/US2012/054120
§ 371 (c)(1),
(2), (4) Date: Mar. 6, 2014

(87) PCT Pub. No.: WO2013/036742
PCT Pub. Date: Mar. 14, 2013

(65) Prior Publication Data
US 2014/0243968 A1    Aug. 28, 2014

Related U.S. Application Data

(63) Continuation of application No. PCT/US2012/054120, filed on Sep. 7, 2012.

(60) Provisional application No. 61/532,847, filed on Sep. 9, 2011.

(51) Int. Cl.
*A61F 2/24*    (2006.01)

(52) U.S. Cl.
CPC ............. *A61F 2/2457* (2013.01); *A61F 2/246* (2013.01); *A61F 2/2466* (2013.01); *A61F 2/2463* (2013.01); *A61F 2230/0054* (2013.01); *A61F 2230/0093* (2013.01); *A61F 2250/0003* (2013.01); *A61F 2250/006* (2013.01)

(58) Field of Classification Search
CPC .............................. A61F 2/2412; A61F 2/2418
USPC .................................................. 623/2.1–2.19
See application file for complete search history.

(56) References Cited

U.S. PATENT DOCUMENTS

| | | | |
|---|---|---|---|
| 6,332,893 B1 * | 12/2001 | Mortier | ............... A61F 2/2454 623/2.1 |
| 6,419,695 B1 | 7/2002 | Gabbay | |
| 6,869,444 B2 | 3/2005 | Gabbay | |
| 7,527,646 B2 | 5/2009 | Rahdert et al. | |
| 7,785,366 B2 | 8/2010 | Maurer et al. | |
| 7,935,144 B2 * | 5/2011 | Robin | ................... A61F 2/2418 623/2.1 |
| 8,070,805 B2 | 12/2011 | Vidlund et al. | |
| 8,092,525 B2 | 1/2012 | Eliasen et al. | |
| 8,114,154 B2 | 2/2012 | Righini et al. | |
| 8,187,299 B2 | 5/2012 | Goldfarb et al. | |
| 8,460,370 B2 | 6/2013 | Zakay et al. | |
| 8,480,732 B2 | 7/2013 | Subramanian | |
| 2003/0130731 A1 | 7/2003 | Vidlund et al. | |

(Continued)

FOREIGN PATENT DOCUMENTS

| | | |
|---|---|---|
| EP | 12829264.6 | 3/2013 |
| WO | 2012103173 A2 | 8/2012 |

*Primary Examiner* — Suzette J Gherbi
(74) *Attorney, Agent, or Firm* — Emory Patent Group

(57) ABSTRACT

The systems and devices and methods relate to surgical and percutaneous repair of heart valve regions. The systems and devices are structured to conform to the desired shape of a specific patient. The devices may include a mounting structure and a valve support onto which leaflets of the valve may coapt or rest. The devices may be structured to be mounted directly onto a leaflet of the valve.

19 Claims, 26 Drawing Sheets

(56) References Cited

U.S. PATENT DOCUMENTS

| | | | |
|---|---|---|---|
| 2004/0148020 A1 | 7/2004 | Vidlund et al. | |
| 2004/0243229 A1* | 12/2004 | Vidlund | A61B 17/00234 623/2.34 |
| 2005/0273160 A1* | 12/2005 | Lashinski | A61F 2/2436 623/1.25 |
| 2007/0005133 A1* | 1/2007 | Lashinski | A61F 2/2418 623/2.17 |
| 2007/0219630 A1* | 9/2007 | Chu | A61F 2/2412 623/2.11 |
| 2007/0255399 A1 | 11/2007 | Eliasen et al. | |
| 2008/039935 A1 | 2/2008 | Buch et al. | |
| 2008/0125860 A1 | 5/2008 | Webler et al. | |
| 2008/0133002 A1* | 6/2008 | Gelbart | A61F 2/2412 623/2.1 |
| 2008/0177381 A1* | 7/2008 | Navia | A61F 2/2418 623/2.11 |
| 2008/0249618 A1 | 10/2008 | Huynh et al. | |
| 2009/0076600 A1 | 3/2009 | Quinn | |
| 2009/0082857 A1* | 3/2009 | Lashinski | A61B 17/0644 623/2.18 |
| 2010/0298929 A1 | 11/2010 | Thornton et al. | |
| 2010/0318184 A1 | 12/2010 | Spence | |
| 2010/0324668 A1 | 12/2010 | Maurer et al. | |
| 2010/0331972 A1* | 12/2010 | Pintor | A61F 2/2409 623/2.11 |
| 2011/0060407 A1 | 3/2011 | Ketai et al. | |
| 2011/0087322 A1* | 4/2011 | Letac | A61F 2/2412 623/2.11 |
| 2011/0093062 A1 | 4/2011 | Cartledge et al. | |
| 2011/0160846 A1* | 6/2011 | Bishop | A61F 2/2418 623/2.11 |
| 2011/0213460 A1* | 9/2011 | Lashinski | A61B 17/0644 623/2.18 |
| 2011/0307055 A1* | 12/2011 | Goldfarb | A61B 17/12 623/2.11 |
| 2012/0078358 A1 | 3/2012 | Vidlund et al. | |
| 2012/0095552 A1* | 4/2012 | Spence | A61F 2/2412 623/2.36 |
| 2012/0143320 A1 | 6/2012 | Eliasen et al. | |

* cited by examiner

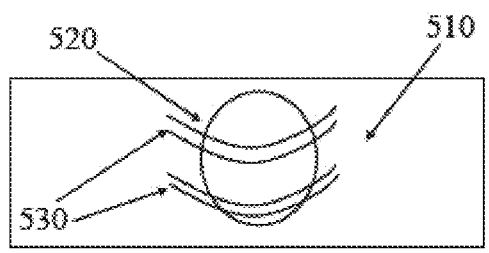
FIG. 5
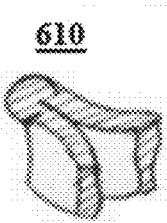 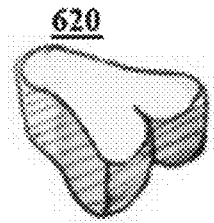 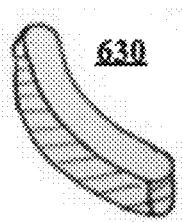 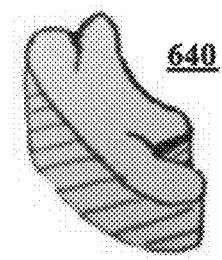
FIG. 6A     FIG. 6B     FIG. 6C     FIG. 6D

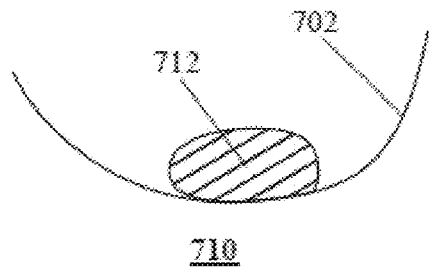
FIG. 7A
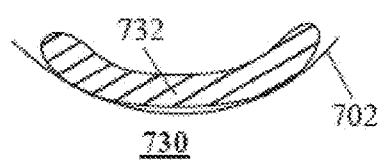
FIG. 7B
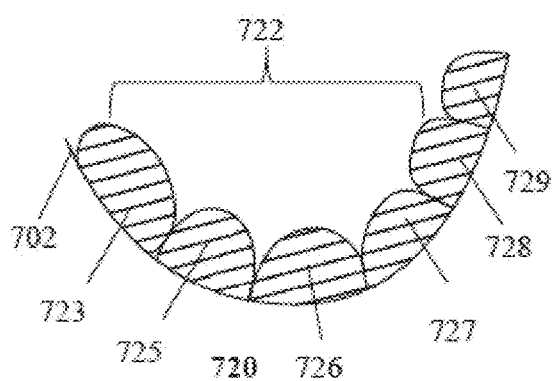
FIG. 7E
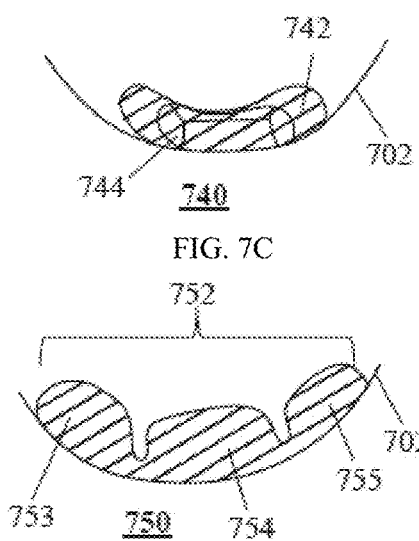
FIG. 7C
FIG. 7D
FIG. 8A
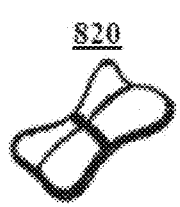
FIG. 8B
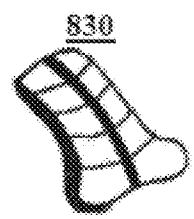
FIG. 8C
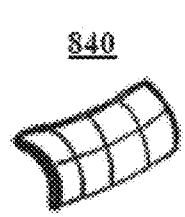
FIG. 8D
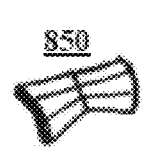
FIG. 8E
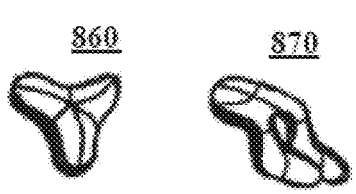
FIG. 8F
FIG. 8G
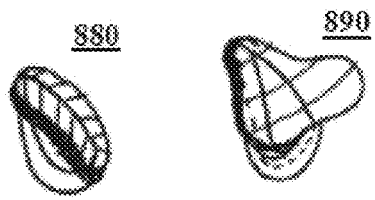
FIG. 8H
FIG. 8I

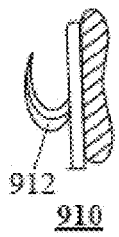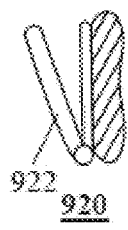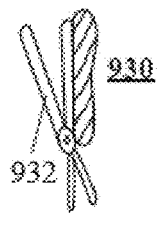
FIG. 9A  FIG. 9B  FIG. 9C  FIG. 9F  FIG. 9G
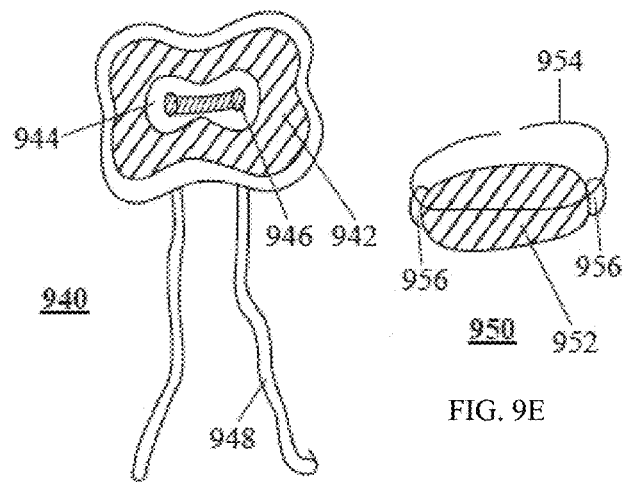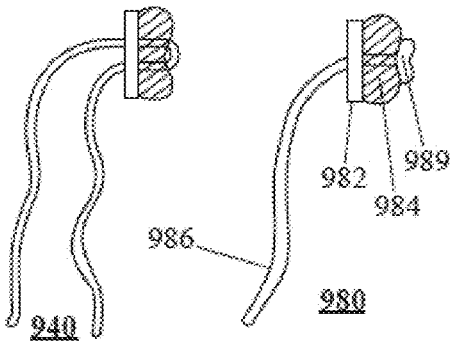
FIG. 9E  FIG. 9H  FIG. 9I
FIG. 9D
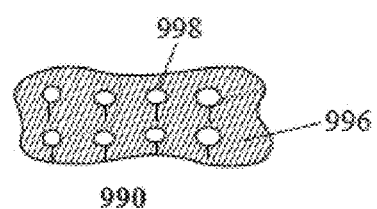
FIG. 9J
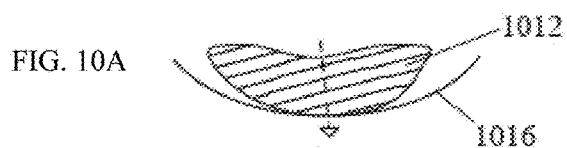
FIG. 10A
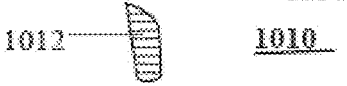
FIG. 10B
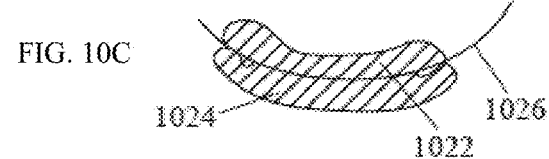
FIG. 10C
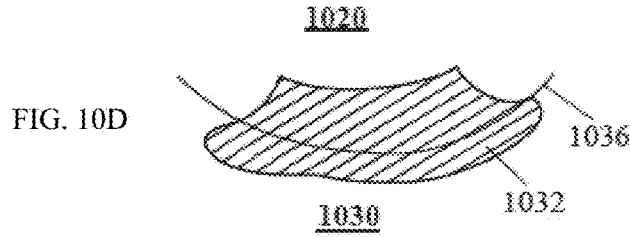
FIG. 10D
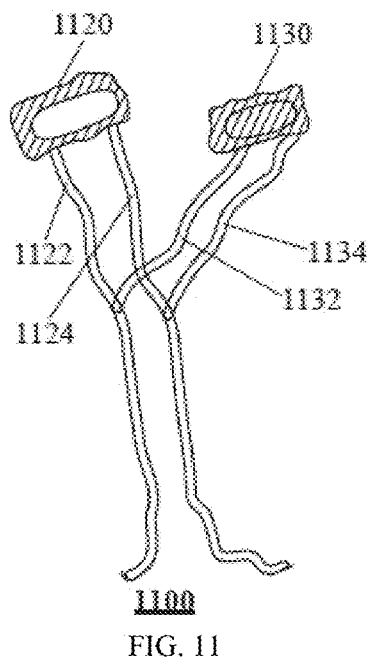
FIG. 11

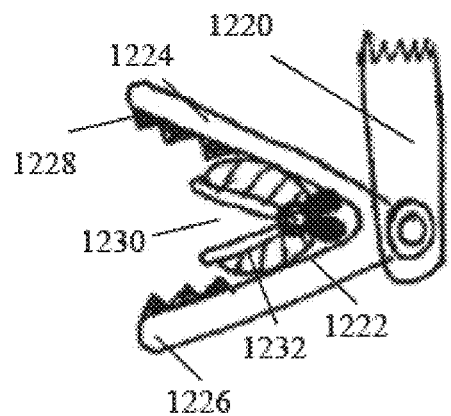
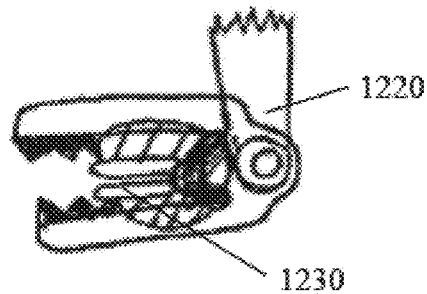
FIG. 12A    FIG. 12B
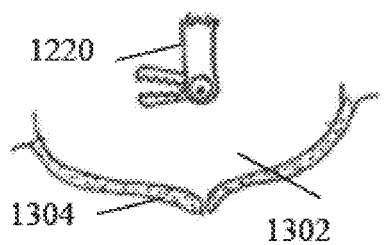
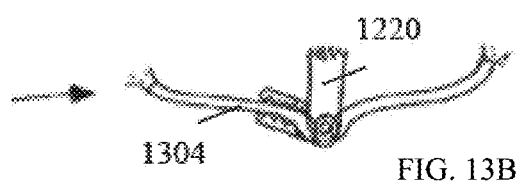
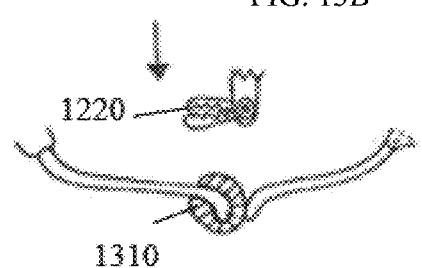
FIG. 13A
FIG. 13B
FIG. 13C

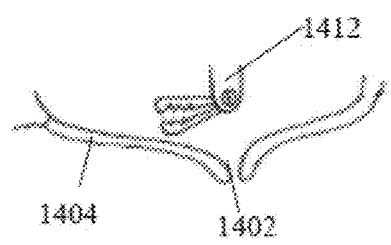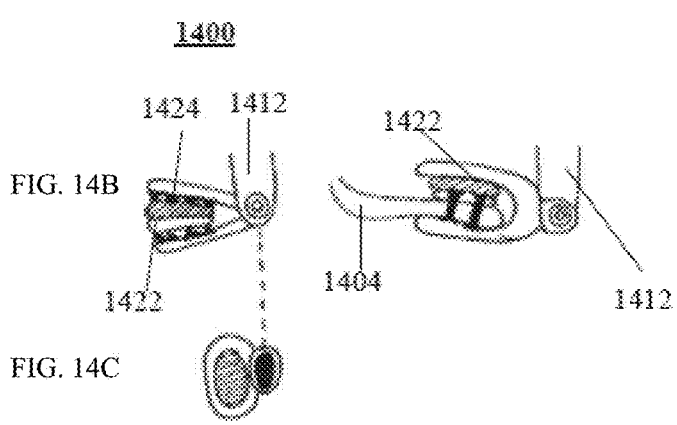
FIG. 14A  FIG. 14D
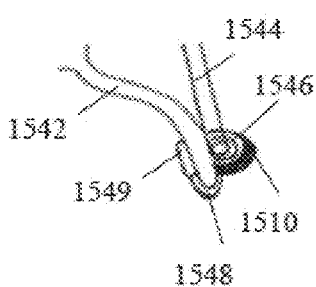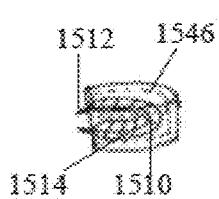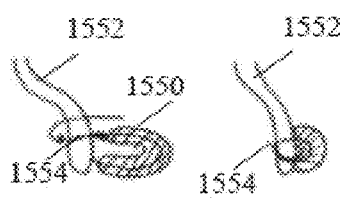
FIG. 15A   FIG. 15B   FIG. 15C   FIG. 15D
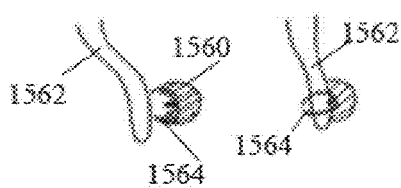
FIG. 15E   FIG. 15F

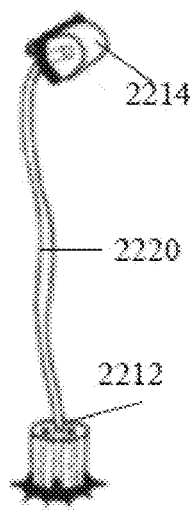
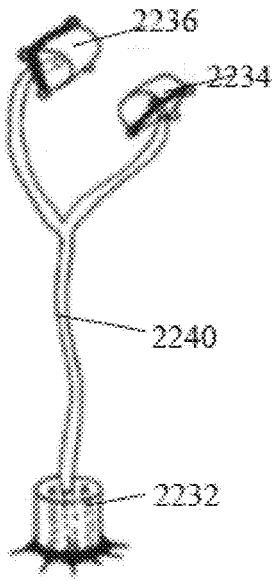
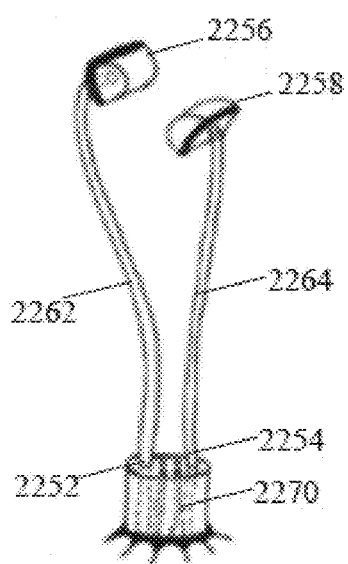
FIG. 22A        FIG. 22B        FIG. 22C
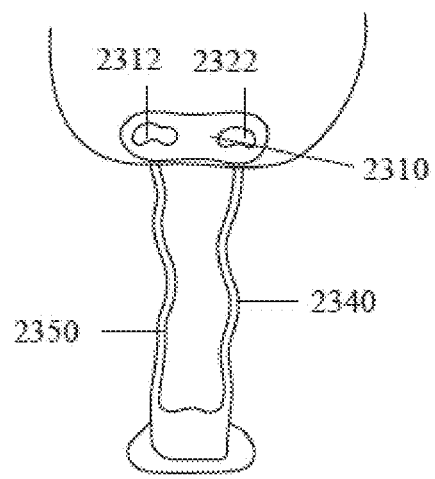
FIG. 23

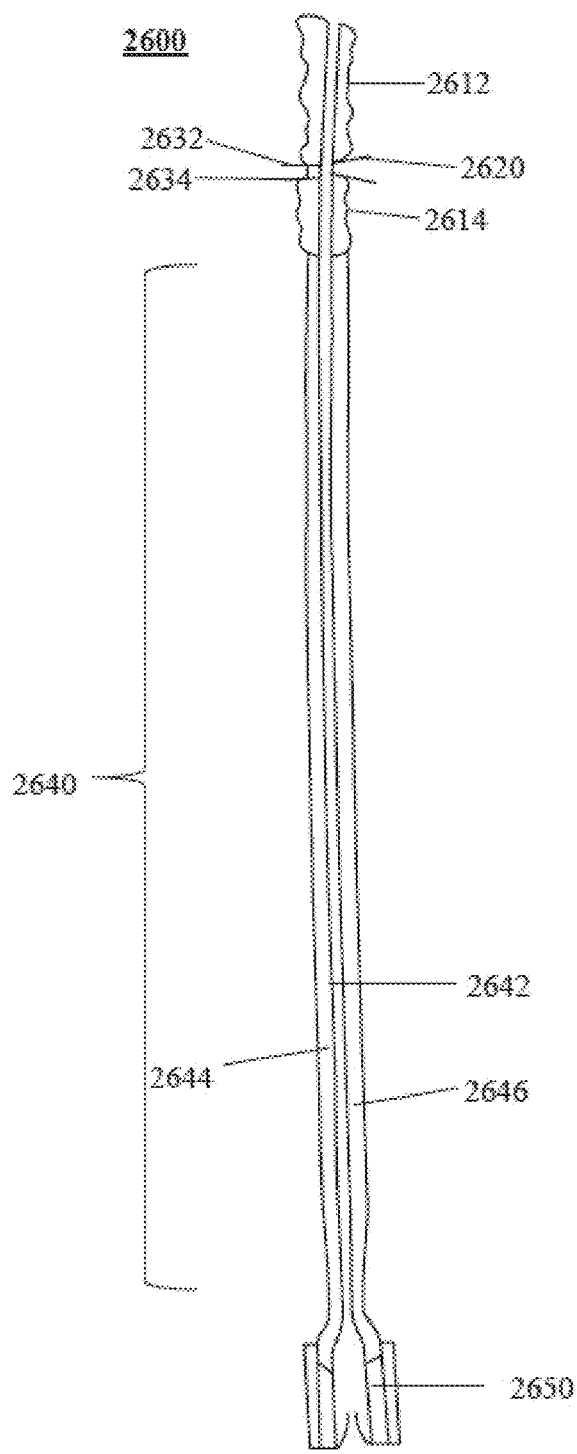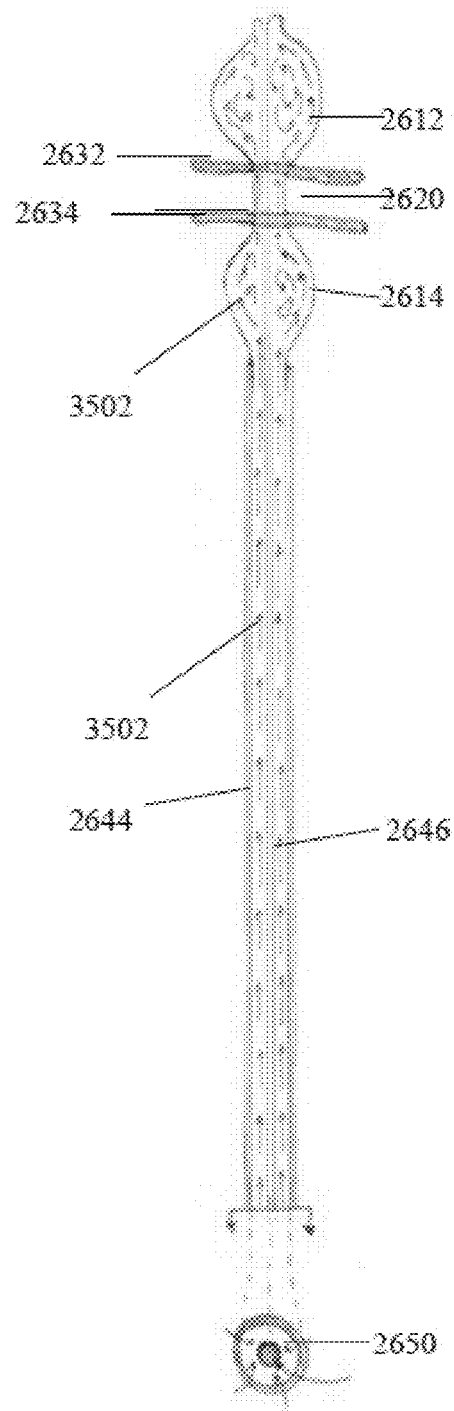
FIG. 26                    FIG. 35

SYSTEMS, DEVICES AND METHODS FOR REPAIR OF HEART VALVE LESIONS

CROSS REFERENCE TO RELATED APPLICATION

This application claims priority to U.S. Provisional Application Ser. No. 61/532,847 filed Sep. 9, 2011, which is hereby incorporated by this reference in its entirety.

FIELD

This disclosure relates to systems, devices and methods for surgical and percutaneous repair of heart valve lesions. In some embodiments, the disclosure relates to devices for repairing a heart valve including a valve support structured to expand and to provide a coaptation surface for the leaflets. The devices may further include a mounting structure structured to mount onto a leaflet. In other embodiments, the disclosure relates to systems including a delivery device structured to deliver the repair devices.

BACKGROUND

Heart valve disorders rank second in all cardiovascular diseases that contribute to mortality in the western and eastern worlds, and impose significant financial burden on healthcare systems. Currently, patients receive either medical treatment or surgical repair or replacement using open heart surgery. Medical treatment is only a medical management option that reduces the symptoms in these patients. However, medical treatment typically only delays the need for more invasive procedure to correct the actual heart valve lesion. Most patients require some invasive procedure to correct the heart valve at some point in their life. In patients who receive surgery, traditional methods of surgery use either mechanical or bio-prosthetic replacement valves in place of native diseased valves, or the native diseased valve is repaired or corrected by manipulating the native valve tissue.

Valve replacement, however, has its drawbacks and has been losing traction as the standard of care. Valve replacement requires lifelong anti-coagulation therapy with mechanical heart valves, and has less than 10 years of durability with the use of bio-prosthetic heart valves.

Valve repair, on the other hand, is becoming more popular as the standard of care. Up to 250,000 valve repair procedures are performed each year in the United States alone. However, the durability of such repairs has been very sub-optimal with persistent or recurrent valve regurgitation occurring in up to 64% of the patients. Valve repair procedures typically fail because of the inflexibility of current valve repair devices, specifically, the inability of the procedure to address different valve defects on a patient specific basis using currently available commercial valve repair devices. Also, the procedure to implant current devices requires arresting the heart, assessing the appropriate device shape and size on a flaccid (non-beating) heart, closing the heart and chest via incisions, and then recovering the patient from cardiopulmonary bypass and anesthesia to assess if the valve repair was successful. Patients often have persistent or recurrent valve leakage when the heart resumes beating, even though complete elimination of regurgitation at the time of the valve surgery on the flaccid heart may have been observed. Thus, such patients present with regurgitation after valve repair surgery and often do not receive any additional care because a second surgery would increase the risk of mortality.

There are valve repair devices and methods that are designed to treat regurgitation. See, e.g., U.S. Pat. No. 8,092,525 issued Jan. 10, 2012 (Eliasen et al.); U.S. patent application Ser. No. 11/258,828 filed Oct. 26, 2005 (Eliasen et al.); U.S. Pat. No. 8,070,805 issued Dec. 6, 2011 (Vidlund et al.); U.S. Pat. No. 8,187,299 issued May 29, 2012 (Goldfarb et al.); U.S. patent application Ser. No. 12/858,935 filed Apr. 18, 2010 (Spence); U.S. patent application Ser. No. 12/626,272 filed Nov. 25, 2009 (Subramanian); and U.S. patent application Ser. No. 12/761,225 filed Apr. 15, 2010 (Zakay et al.). However, these devices are generally not structured to be adjusted and adapted to different valve defects on a patient specific basis.

Thus, there is a need for valve repair devices and methods that address the patient variability in heart valve structure and function. Specifically, there is a need for beating heart adjustable devices that conform to the desired shape in individual patients at the time of surgery, or acutely after surgery or several years after surgery.

SUMMARY

The disclosure relates to devices, systems and methods for surgical and percutaneous repair of valves. In some embodiments, the disclosure may relate to a device structured to be implanted to repair a valve. The device may include a valve support. In some embodiments, the device may further include a mounting structure. The mounting structure may be structured to mount the device to a leaflet. In some embodiments, the mounting structure may be structured to support the device with respect to the leaflet. In some embodiments, the repair device may be structured to provide a coaption surface for the valve leaflets.

In some embodiments, the valve support may be structured to expand after the device is implanted. The valve support may be structured to be adjustably expanded. In some embodiments, the valve support may be structured to expand past an edge or boundary of the leaflet. In some embodiments, the valve support may include a balloon. In other embodiments, the valve support may include a permeable membrane. The permeable membrane may have a predetermined porosity. The permeable membrane may be structured to have a predetermined amount of expansion. The expansion may be based on the predetermined porosity. In some embodiments, the device may include more than one valve support.

In some embodiments, the valve support may be disposed on the mounting structure. In some embodiments, the device may include at least one valve support disposed on the mounting structure. In other embodiments, the device may include more than one valve support disposed on the mounting structure. In other embodiments, the mounting structure may be completely encased by the valve support. In other embodiments, the mounting structure may be partially encased by the valve support.

In some embodiments, the mounting structure may include at least one surface. The surface may be structured to be disposed directly on a leaflet. The surface may include a woven material structured to allow invasion and growth of cells. In other embodiments, the mounting structure may include a shape memory alloy. The mounting structure may include more than one surface.

In some embodiments, the mounting structure may include at least one lumen. The mounting structure may include a double lumen. In some embodiments, the mounting structure may include an anchor surface and an extending member. In some embodiments, the mounting structure may be a needle structured to puncture a leaflet.

In some embodiments, the device may include a connector that is structured to secure or attach the device to a leaflet and/or cardiac tissue. In some embodiments, the connector may include a tensioned member structured to clamp the leaflet between the tensioned member and the mounting structure. In some embodiments, the device may include at least one opening structured for a connecting member. The connecting member may be at least one artificial chord structured to attach the device to the leaflet and to a myocardium distal from a leaflet. In some embodiments, the connector may include at least one protruding member or extending member structured to pierce the leaflet. In some embodiments, the connector may include a hook structured to pierce the leaflet. In some embodiments, the connector may be a lumen or tube.

In some embodiments, the disclosure may relate to device for repairing a heart valve. The device may include a valve support and a mounting structure structured to support the device with respect to a leaflet. In some embodiments, the device may further include a hollow tube that extends from the valve support to a port that is structured to deliver fluid to expand the valve support. In some embodiments, the valve support may completely encase the mounting structure. The mounting structure may further include an anchor and an extending member that extends with the hollow tube. In some embodiments, the hollow tube may be flexible. In some embodiments, the tube may include a valve structured for injection of fluid.

In some embodiments, the disclosure may relate to a system for repairing a valve. The system may include more than one repair device, each repair device being structured to mount onto different leaflets of the valve. The repair device may include at least one valve support. In other embodiments, the repair device may include more than one valve support. The repair device may further include a mounting structure structured to support or mount the each device to a leaflet.

In some embodiments, the system may further include a port. In some embodiments, each of the repair devices may further include an extending member that extends from the valve support to a port. In some embodiments, each extending member may converge to a single extending member that connects to the port. In other embodiments, each extending member individually connects to the port. The port may further include a fluid conduit structured to inject saline to each valve support. In some embodiments, the port may be structured to be disposed on an access site of the heart. The port may be structured to be inserted into a myocardium.

In some embodiments, the system may include artificial chordae. The chordae may be structured to anchor the repair device to the leaflet and to secure to the port.

In some embodiments, the disclosure may relate to a device that includes at least one valve support; at least one mounting structure configured to be disposed on a surface a leaflet, wherein the valve support is disposed on the mounting structure mounting structure; and a connector that extends from the valve support to a port.

In some embodiments, the disclosure may relate to a device that include at least two valve supports, at least one valve support being disposed on an atrial side and a ventricular side of a leaflet; and at least two mounting structures structured to be directly disposed on a surface of a leaflet.

In some embodiments, the disclosure may relate to a kit. The kit may include at least one valve support and mounting structure. In some embodiments, the kit may include a plurality of valve supports. The valve supports may be of different sizes and shapes. In some embodiments, the valve supports may be of different materials. In some embodiments, the kit may include a plurality of mounting structures. The mounting structures may be of different sizes and shapes. In some embodiments, the mounting structures may be of different materials. In some embodiments, the kit may further include a port. In some embodiments, the kit may include a valve.

DESCRIPTION OF THE DRAWINGS

The disclosure can be better understood with the reference to the following drawings and description. The components in the figures are not necessarily to scale, emphasis being placed upon illustrating the principles of the disclosure.

FIG. 5 shows a repair device according to embodiments;

FIGS. 6(a)-(d) show embodiments of a repair device;

FIGS. 7(a)-(e) show embodiments of a repair device;

FIGS. 8(a)-(i) show embodiments of a repair device;

FIGS. 9(a)-(j) show embodiments of a repair device;

FIGS. 10(a)-(d) show embodiments of a repair device;

FIG. 11 shows an embodiment of a repair device;

FIGS. 12(a) and (b) shows an embodiment of a delivery device;

FIG. 13(a)-(c) show methods of implanting a repair device with a delivery device according to embodiments;

FIGS. 14(a)-(d) show a method of implanting a repair device with a delivery device according to embodiments;

FIGS. 15(a)-(f) show methods of implanting a repair device with a delivery device according to embodiments;

FIGS. 22(a)-(c) show a repair device according to embodiments;

FIG. 23 shows an implanted repair device according to embodiments;

FIG. 26 shows a repair device according to embodiments;

FIG. 35 shows a repair device according to embodiments being expanded;

DESCRIPTION OF THE EMBODIMENTS

The disclosed devices, methods and systems specifically address the patient variability in heart valve structure, function and the need for beating heart adjustable devices that conform to the desired shape in individual patients at the time of surgery, acutely after surgery or several years after surgery. It will be understood that the valve repair devices disclosed, unless otherwise noted, may be implanted in patients undergoing first-time surgery; or these devices can be implanted in patients who had a failure of a previous repair. Also, unless otherwise noted, the devices disclosed may be implanted using surgical, minimally invasive or percutaneous techniques or using traditional open-heart surgical techniques. These devices are structured to be implanted into the cardiac structure under image guidance, repositionable during implantation, and retrievable immediately or several years after surgery. Image guidance may include but is not limited to ultrasound, MRI, CT, and echocardiogram.

It will be understood that the devices, methods and systems are not limited to the valves and leaflets shown in the figures. It will be understood that it is within one of ordinary skill to modify the devices, systems, and methods for any one leaflet or any combination of leaflets of any heart valve.

The disclosed valve repair devices may reduce or eliminate regurgitation by enabling the overlap or coaptation of the native valve leaflets onto an artificial surface that is conformable to a desired shape as determined by the user at the time of implantation or at a time after implantation. The devices may also eliminate any blood leakage through the valve by sealing the orifice created by the non-coaptation of the leaflets. Additionally, the devices can support for a flail or prolapsing leaflet.

Figure 1:
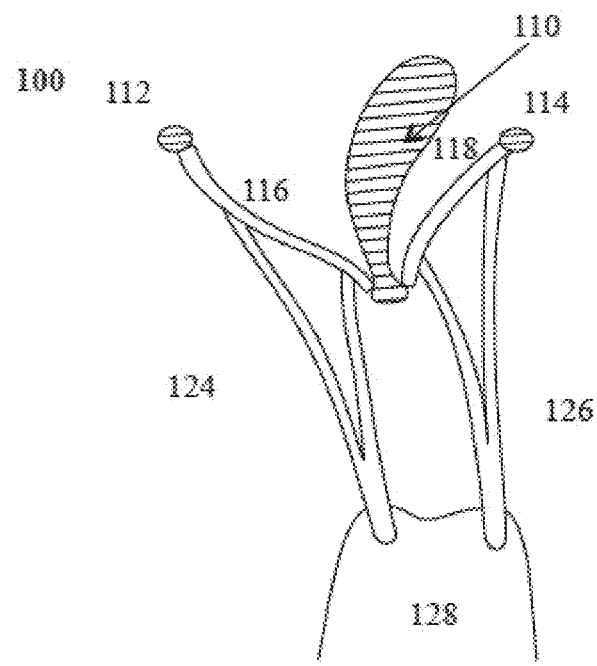
FIG. 1 shows an example of mitral valve deficiency.

FIG. 1 shows an example of mitral valve insufficiency. Specifically, FIG. 1 shows a diagram 100 of a mitral valve 100 (mitral annulus (MA) 112; anterior leaflet (AL) 116; posterior leaflet (PL) 118; chordae tendineae (CT) 124 and 126; posterior-medial papillary muscle (PPM) 128); and antero-lateral papillary muscle (APM) 132) that does not completely close or coapt when the left ventricle contracts thus causing mitral regurgitation. This allows blood to backflow (110) into the left atrium resulting in left ventricular overload. This added workload, if not corrected, may eventually cause heart failure.

Figure 2:
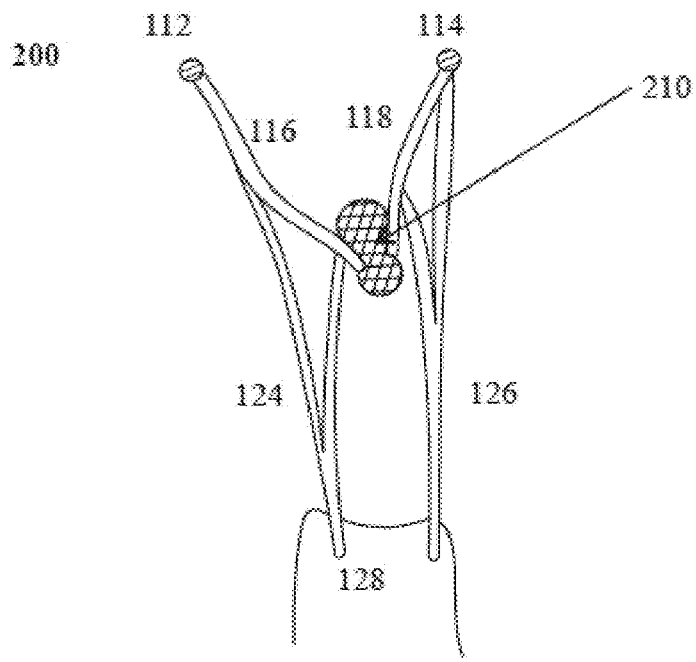
FIG. 2 shows a repair device according to an embodiment implanted onto a valve.
Figure 3:
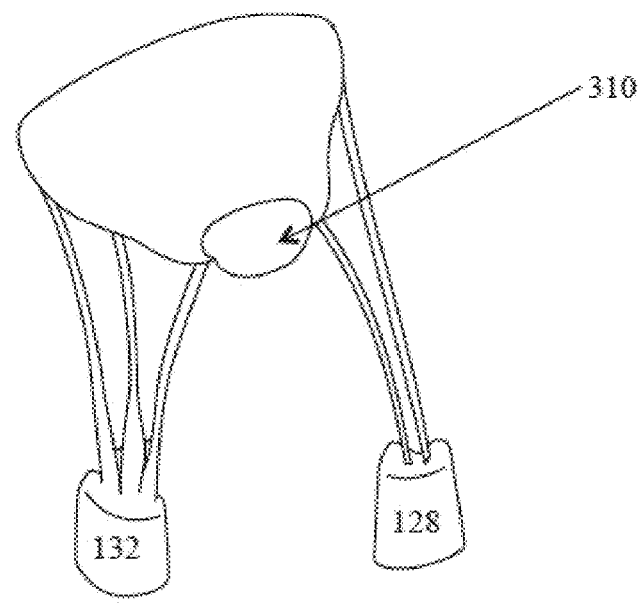
FIG. 3 shows a repair device according to an embodiment implanted onto a valve.
Figure 4:
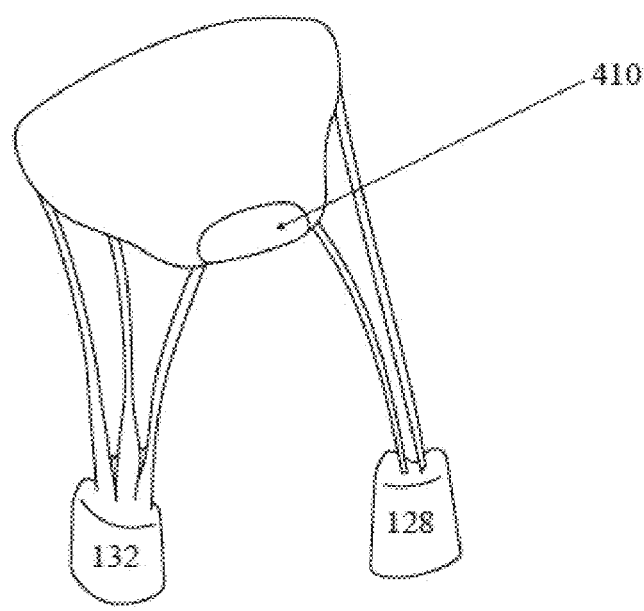
FIG. 4 shows a repair device according to an embodiment implanted onto a valve.

FIGS. 2-4 show examples of the valve repair devices according to embodiments mounted on a leaflet of the mitral valve 100 that had mitral regurgitation as shown in FIG. 1. As shown in diagrams 200, 300, and 400, the devices may include at least one valve support (also referred to as "valve support") (210, 310, 410, respectively) that is structured to expand and to provide a coaptation surface for the leaflets. The valve support may be structured to increase or expand the surface area of one or more leaflets thus increasing the surface area for coaptation. The valve support closes the gap between the leaflets. As shown in the figures, when implanted with the valve support (in an expanded state), the leaflets properly coapt thus eliminating or reducing mitral regurgitation.

The valve support may have any shape. FIGS. 2-4 show some examples of the shapes of the valve support according to embodiments. The shapes, the numbers, the configurations, etc., are not limited to those shown in these figures as well as any of the figures.

The shape of the valve support may be determined based on the anatomy of the valve as determined by medical imaging techniques and methods. The placement of the device may also be determined and/or confirmed by medical imaging devices. The medical imaging devices include but are limited to, ultrasound and echocardiogram.

According to some embodiments, the devices may include at least one valve support structured to expand to provide a coaptation surface for at least one leaflet. In some embodiments, the at least one valve support may be configured to be disposed on a surface of the leaflet. The valve support may be of any shape in an initial (unexpanded) position. The valve support may also be structured to have the same or different shape when in the expanded position. The shapes of the valve support may correspond to the anatomy of the valve to be repaired.

In some embodiments, one or more valve supports may be structured to extend to the boundary of a leaflet. FIGS. 10(a) and (b) show top and side views of a valve support that may be structured to extend to the boundary of a leaflet 1016. In other embodiments, one or more of valve supports may be structured to extend past the boundary of the leaflet. FIGS. 10(c) and (d) show a top view of devices 1020 and 1030 that include valve supports that may be structured to extend past the boundary of the leaflet. FIG. 10(c) shows a top view of two valve supports 1022 and 1024 that may be attached to each other or integrated. At least one of the valve supports may extend past the boundary of a leaflet 1026. FIG. 10(d) shows a top view of a device 1030 that includes (single) valve support 1032 that may be structured to extend past the boundary of a leaflet 1036.

According to some embodiments, one or more valve supports may have a circular shape in an initial (unexpanded) position and/or expanded position. According to other embodiments, the valve support may also have other shapes in an unexpanded position and/or expanded position. FIGS. 2-5 and 6(a)-(d) show examples of different shapes of the valve support(s) according to embodiments. For example, in some embodiments, the valve support 510 may have a circular shape, as shown in FIG. 5. In certain embodiments, the valve support may have a v-shape (e.g., support 610 shown in FIG. 6(a)), a different v-shape (support 620), an elongated shape (e.g., support 630 shown in FIG. 6(c)), a mushroom-like shape (e.g., support 640 shown in FIG. 6(d)), among others, or some combination thereof. It will be understood that the at least one valve support is not limited to those shapes and may be of any shape.

In some embodiments, the device may include one valve support. FIGS. 7(a)-(c) show examples of a device including one valve support. FIGS. 7(a) and (b) show devices 710 and 730 having a circular valve support 712 and an elongated valve support 732 with respect to a leaflet 702, respectively. FIG. 7(c) shows a device 740 having an elongated valve support 744 that surrounds a mounting structure (e.g., a lumen) 742. Embodiments of the mounting structure are further described below, for example, with respect to FIG. 8.

In certain embodiments, the device may include more than one valve support. The device may include any number of valve supports. In some embodiments, the device may include more than one valve support of the same material and shape. In other embodiments, the device may include more than valve support of any combination of materials and shapes. In some embodiments, the more than one valve support may be disposed adjacent to each other with respect to a (same) side or surface (e.g., an atrial side) of a leaflet. FIGS. 7(d) and (e) shows examples of devices according to these embodiments.

In certain embodiments, the more than one valve support may be additionally or alternatively disposed on opposing surfaces or sides of a leaflet, for example, as shown in and described with respect to FIGS. 26 through 37.

In some embodiments, the valve supports may be structured to be collectively expanded together at the same time and/or sequentially. FIG. 7(d) shows a device 750 that includes a plurality of separate valve supports 752 disposed on one side of a leaflet 702. Although the device 750 shows three valve supports 753, 754, and 755, the device 750 may include any number of valve supports. For example, the device 750 may include two, four, five, or more than six valve supports.

In other embodiments, the valve supports may be separated so that they are structured to be individually expanded. FIG. 7(e) shows a device 720 including an integrated valve support 722 disposed on one side of a leaflet 702. Although the device 720 shows six valves supports 723, 725, 726, 727, 728, and 729. The device 720 may include any number of valve supports. For example, valve support 722 may include two, three, four, five, or more than six valve supports.

In some embodiments, the valve support may be configured to be expanded after implantation onto a leaflet. In some embodiments, the valve support may include a flexible, impermeable membrane structured to expand when filled with fluid and/or a gas (e.g., air). In some embodiments, the flexible membrane may be a balloon. The balloon may be made of any known biocompatible silicone or polymer or polymers with shape memory properties. In some embodiments, the balloon may be similar to an angioplasty balloon.

In some embodiments, the device may further include at least one receiving member that extends from the valve support structured to receive the fluid or the air. In some embodiments, the fluid may include but is not limited to saline. The device may include more than one receiving member. The receiving member may be tubing or a lumen that is integrated with or attached to a connector site, such as an opening provided within the valve support. FIG. 11 shows an example of a device 1100 having two valve supports 1120 and 1130, each body 1120 and 1130 including two receiving members 1122 and 1124, and 1132 and 1134, respectively. The receiving member may remain with the repair device after implantation or may be removably disposed.

In some embodiments, the receiving member may be configured to also fixedly dispose the valve support to a leaflet. The receiving member may be configured to attach to a surface of a leaflet and/or a surface of a cardiac wall, such as a ventricular apex. In some embodiments, the receiving member may be integrated or a part of a connector and/or the valve support(s) according to embodiments.

In certain embodiments, the valve support may be configured to be self-expanding. The valve support may include a permeable membrane structured to expand when in contact with bodily fluid such as a blood. In some embodiments, the permeable membrane may have a predetermined porosity. The predetermined porosity may be chosen based on the amount of expansion desired. When exposed to a fluid, the permeable membrane may absorb and retain the fluid of a known volume based on the porosity and thus limit the expansion to a desired level. The permeable membrane may also have a predetermined amount of expansion. The permeable membrane may include but is not limited to a hydrophilic material, such as hydrophilic protein or a biocompatible gelatin In other embodiments, the valve support may include shape memory alloys such as Nitinol® or treated biological tissue. For example, the tissue may be treated with glutaraldehyde, genipin or other solutions that improve the durability of the un-treated biological tissue.

The device may include the more than one valve support that has the same type, shape, size, and material, has different type, shape, size, and material, or some combination thereof.

In some embodiments, the devices may further include at least one mounting structure (also referred to as a "mounting frame"). In some embodiments, the mounting structure may be structured to support and/or secure the at least one valve support with respect to a surface of a leaflet. In some embodiments, the mounting structure may be structured to anchor or mount, the at least one valve support to the leaflet. In further embodiments, the mounting structure may be structured to attach the at least one valve support to or be directly disposed on a leaflet.

In some embodiments, the devices may include one mounting structure. In other embodiments, the devices may include more than one mounting structure. The mounting structures may be the same, different, and/or some combination thereof.

In some embodiments, the mounting structure may be configured to be disposed on at least one external surface of a leaflet. FIGS. 8, 9 and 12 through 15 show example of devices according to these embodiments.

In some embodiments, the mounting structure may include one surface configured to be externally disposed on one side of a leaflet. In other embodiments, the mounting surface may include more than one surface configured to be externally disposed on more than one side of a leaflet. The mounting structure may include two opposing surfaces and an opening. The two opposing surfaces may partially or completely surround an opening structured to receive and surround the external surface leaflet tissue.

The mounting structure may include surface(s) of any shape. The mounting structure may be symmetrical or asymmetrical. The mounting structure may include any combination of plurality of surfaces of different shapes or the same shapes. In some embodiments, the shape of the mounting structure may correspond to the anatomy of the leaflet.

FIGS. 8(a)-(i) show examples of mounting structures. According to some embodiments, the at least one mounting structure may have an elongated circular shape (e.g., structure 810 shown in FIG. 8(a)); have a square-like shape with rounded edges and narrower middle (e.g., structure 820 shown in FIG. 8(b)); a rectangular-like shape having a rounded edge (e.g., structure 830 shown in FIG. 8(c)); a rectangular shape (e.g., structure 840 shown in FIG. 8(d)); an elongated shape that tapers toward the middle (e.g., structure 830 shown in FIG. 8(e)); and a triangular shape (e.g., suture 860 shown in FIG. 8(f)).

In some embodiments, the mounting structure may have two opposing surfaces that extend from a main surface so as to form an opening that is structured to partially surround a leaflet when mounted (e.g., structure 870 shown in FIG. 8(g)); an opposing circular surface attached to a square-like surface so as to form an opening to fully surround a leaflet when mounted (e.g., structure 880 shown in FIG. 8(h)); and an opposing circular surface attached to a triangular-like surface so as to form an opening to fully surround a leaflet when mounted (e.g., structure 890 shown in FIG. 8(i)).

In some embodiments, the mounting structure may be made of a single material. In other embodiments, the mounting structure may be made of a plurality of different materials. In some embodiments, the mounting structure may be made of a flexible biocompatible material. In some embodiments, the mounting structure may be made of a biocompatible composite or woven fabric material that allows for invasion and growth of cells. The material may include but is not limited to felt. In some embodiments, the mounting structure may be made of shape-memory alloy, such as Nitinol®. In other embodiments, the mounting structure may be made of treated biological tissue. For example, the tissue may be made with Polytetrafluoroethylene (PTFE) or treated with glutaraldehyde. The mounting structure may also be made of an elastomer, such as EPT.

In some embodiments, the mounting structure may include a plurality of layers of the same or different materials.

In some embodiments, the devices may include at least one barrier layer to prevent infection and/or promote in-growth. In some embodiments, the mounting structure may include a barrier layer. In other embodiments, the mounting structure may include at least one barrier layer configured to be disposed between the at least one valve support and an external surface of a leaflet. In some embodiments, the barrier layer may be a biocompatible material, for example, polyester or a felt-like material.

In some embodiments, the repair device may include a lumen. The repair device may include a single lumen or a plurality of lumens. The repair device may include a double lumen. In some embodiments, the at least one lumen may be made of the same material as the valve support. In other embodiments, the at least one lumen may be made of a different material. The at least one lumen may be made of any known biocompatible material, such as an elastomer.

In some embodiments, at least one valve support may be disposed on a side of the mounting structure. At least one valve support may be disposed anywhere along (a surface) of the mounting structure. At least one valve support may be disposed along a portion and/or the entire length of the mounting structure. At least one valve support may be fixedly disposed on the mounting structure by at least one fastener. In other embodiments, at least one valve support may be fixedly disposed on the mounting structure by more than one fastener. The fasteners may be the same or different. The fastener(s) may include but are not limited to biocompatible sutures, and biocompatible adhesive or an epoxy. The sutures may be artificial chordae. The sutures may include but are not limited to filaments such as ePTFE and GORE-TEX™ sutures. In some embodiments, the fasteners may puncture at least one valve support. In other embodiments, the fasteners may surround the valve support (without puncturing it).

FIG. 5 shows an example of a valve support 510 mounted on a mounting structure 520 by fasteners 530. The fasteners shown in FIG. 5 are several sets of sutures. The fastener may include one set or a plurality of sets of sutures around the valve support.

Figures 19A, 19B:
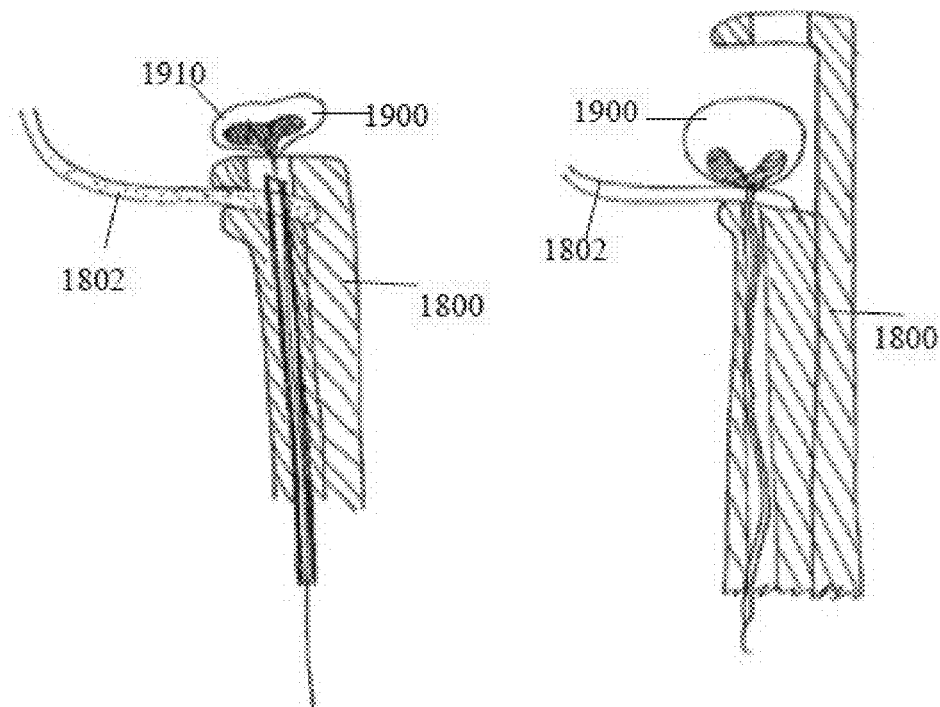
FIGS. 19(a) and (b) show additional steps of a method of implanting a repair device with a delivery device according to embodiments.
Figure 20:
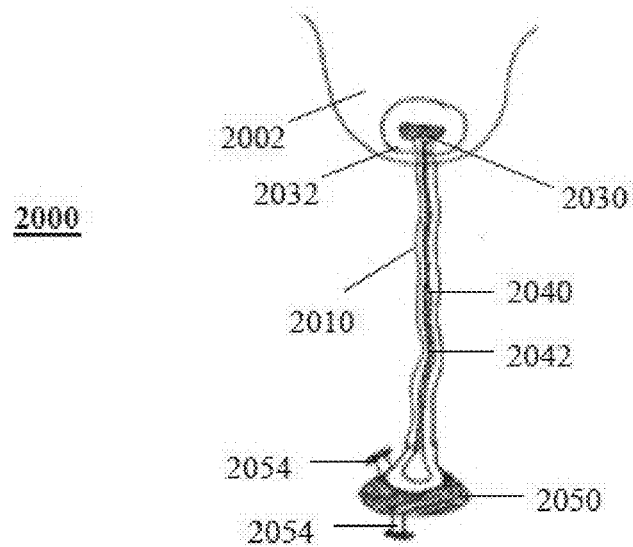
FIG. 20 shows an implanted repair device according to embodiments.

In other embodiments, the mounting structure may be partially or completely encased or surrounded by the valve support. In some embodiments, the mounting structure may be a lumen surrounded by the valve support, for example, as shown in device 740 shown in FIG. 7(c). In other embodiments, the mounting structure may include a structural anchor or support surface and may be contained within the valve support, as shown in FIGS. 19 and 20. In some embodiments, the mounting structure may further include an extending member structured to extend along the valve support, as shown in FIGS. 19 and 20.

According to some embodiments, the devices may further include at least one connector structured to fixedly dispose and/or attach the devices to the leaflet. In some embodiments, the connector may be The devices may include any number of connectors. In some embodiments, the devices may include one connector. In other embodiments, the devices may include more than one connector. FIGS. 9(a)-(i) show examples of devices with different connectors. It will be understood that the connectors are not limited to those shown in the figures.

In some embodiments, the connectors may be disposed on the mounting structure and be disposed to penetrate the leaflet. For example, FIG. 9(j) shows a device 990 that includes a mounting structure 996 having a plurality of connectors 998. In some embodiments, the connectors may be directly disposed on the mounting structure(s). The connectors may be disposed on one surface of the mounting structure. The connectors may be disposed at the ends of the mounting structure. In some embodiments, the connectors may be a part of, may be integrated with the mounting structure, may be affixed to the mounting structure, and/or some combination thereof.

In some embodiments, the connector(s) may be disposed on and/or extend partially or completely within at least one valve support and/or mounting structure. For example, FIG. 9(e) shows a device 950 that includes a valve support 952 and a connector 954 that extends through the valve support 952. The device 950 may further include a mounting structure 956 disposed on either side of a valve support 952. A device according to these embodiments may be structured for a suture to pass through each mounting structure and the valve support.

In other embodiments, the device a valve support and at least one connector that extend through the valve support. FIG. 15(b) through (f) shows examples of devices according to different embodiments. FIG. 15(b) shows a device 1510 may include a valve support 1514 and a connector 1512 that extends through the valve support 1514. FIGS. 15(c) and (d), and (e) and (f) show devices 1550 and 1560 implanted on a valve, respectively according to certain embodiments. FIGS. 15(c) and (d) show a device 1550 that may include a connector 1554 configured to completely surround a leaflet 1552. FIGS. 15(e) and (f) show a device 1560 that may include a connector 1564 configured to partially surround a leaflet 1562.

In some embodiments, the repair device may include one or more connector sites configured to receive a connector. In some embodiments, the connector site may be structured to receive a connector, for example, a suture(s) to be pulled or threaded through or a metal or alloy wire structured to puncture the leaflet, such as a needle. In some embodiments, the connector site may include at least one opening provided within the at least one valve support and/or at least one mounting structure. In some embodiments, the sutures may any one of the sutures discussed above with respect to fasteners. In other embodiments, the sutures may be any sutures. The sutures may be the same or different as the sutures that may be used as fasteners.

In some embodiments, the at least one connector site may be parallel with the leaflet to be sutured so that the opening may correspond to the puncture in the leaflet. FIGS. 9(d), (h) and (i) show examples of devices having at least one opening structured for connector, such as sutures. The sutures are shown as threaded or pulled through the openings for illustrative purposes. FIGS. 9(d) and 9(h) show front and side views of a device 940 that includes a mounting structure 942 including two openings 944, 946 structured for a connector (e.g., suture) 948. FIG. 9(i) shows a device 980 that includes a mounting structure 982, a valve support 984, an opening 986 provided within the mounting structure 982 and the valve support 984, structured for a connector (e.g., suture) 988. The device 900 may further include a securing member 989 that may be disposed above or on top of a valve support 984 and may be parallel to the mounting structure 982. The suture may be attached to the securing member. The securing member may be structured to secure the position of artificial member as well as secure the suture. The membrane may be made as the same material or different material as the mounting structure.

In other embodiments, the connector may include at least one protruding member. The connector may include one or any number of protruding members. The protruding member(s) may be structured to puncture or to be implanted directly into a leaflet. The protruding member may be made of a biocompatible polymer, alloy or metal material. The metal may be a memory-shape alloy, such as Nitinol®. The protruding member(s) may be of any shape. FIGS. 9a), (f) and (g) show examples of devices that include protruding members. FIG. 15 shows another example of a protruding member.

In some embodiments, a device 910 may include a connector 912 having a hook-like shape, as shown in FIG. 9(a). In other embodiments, the device may include a plurality of connectors. For example, a device 970 may include connectors 972 that are straight protruding members, as shown in FIG. 9(g). In other embodiments, a device 960 may include connectors 962 that are angled and cross as shown in FIG. 9(f).

In some embodiments, the device may include a connector that is structured to surround an external surface of a leaflet, for example, by clamping a leaflet. The connector may be a tensioned member that is structured to move between an open and a closed position. The connector may have a shape that corresponds to the shape of the mounting structure. In some embodiments, the connector may be an elongated member. The connector may be a separate member that is attached to the mounting structure in a tensioned manner. The connector may be attached to the mounting structure by a tensioned fastener. FIGS. 9(b) and (c) show examples of devices according to these embodiments. As shown in FIGS. 9(b) and (c), devices 920 and 930 may include tensioned connectors 922 and 932, respectively.

According to some embodiments, the devices may be structured to be implanted using percutaneous surgery methods. In some embodiments, the disclosure relates to delivery devices structured to implant or mount the devices onto a leaflet of the valve. In some embodiments, the disclosure relates to systems that include the delivery devices and the devices. According to embodiments, the delivery device may depend on the device to be implanted and the point of access. The systems may be structured for atrial access. In other embodiments, the systems may be structured for ventricular access. The access may be apical.

According to embodiments, the delivery devices may be used with a catheter. In other embodiments, the delivery devices may be used with medical imaging for positioning. The medical imaging may include but are not limited to ultrasound, MRI, and CT.

FIGS. 12-15 show examples of delivery devices for implanting the valve repair devices according to embodiments. FIGS. 12(a) and (b) show a delivery device 1220 in an open position and in a closed position, respectively. The delivery device 1220 may include a recess 1222 for the valve repair devices, such as valve repair device 1230. The recess 1222 may be structured so that the valve delivery device may open and close with the delivery device. The recess 1222 may also be structured so that the valve delivery device stays within the delivery device until implantation. The delivery device may include two tensioned extending members 1224, 1226. Each of the members may include protruding members 1228, such as teeth, structured to assert pressure against the leaflet. The delivery device 1220 may be used with other valve repair devices and is not limited to the device shown in the figures. The valve repair devices may include a valve support 1232 that is either of permeable membrane or a balloon. FIGS. 13 and 14 may be preferably used with a valve support that is a permeable membrane.

FIGS. 13(a)-(c) show a method of implanting a repair device using the delivery device 1220 shown in FIG. 12. In step 1, the delivery device 1220 may be introduced into a valve 1302, as shown in for example, FIG. 13(a). Next, in step 2, the delivery device 1220 may be positioned to clamp around a leaflet 1304 so as to implant or deliver the valve repair device 1310, for example, as shown in FIG. 13(b). Next, in step 3, the valve repair device 1310 is implanted on the leaflet 1304, for example, as shown in FIG. 13(c).

FIGS. 14 (a), (b), and (d) show another method of implanting a repair device using a delivery device according to different embodiments. In step 1, a delivery device 1412 may be introduced into a valve 1402, for example, shown in FIG. 14(a). Next, in step 2, the delivery device 1412 may be positioned to clamp around a valve leaflet 1404 so as to implant or deliver at valve repair device 1422 that includes tensioned extending member 1424, for example, as shown in FIG. 14(b). As shown in the top view shown in FIG. 14(c), the surface area of tensioned extending members 1424 may be wide enough to capture a large area of the leaflet. Next, in step 3, for example, as shown in FIG. 14(d), the valve repair device 1422 may be implanted on the leaflet 1404.

FIGS. 15(*a*)-(*e*) show another method of implanting a repair device using a delivery device according to different embodiments. In some embodiments, as shown in example FIG. 15(*a*), the delivery device 1544 may include a protruding portion 1546 having a recess to secure a repair device until implantation and an opposing portion. The protruding portion 1546 and a curved portion 1548 may be structured to clamp a leaflet 1542. The curved portion 1548 may extend from the protruding portion 1546 and may be structured to surround a leaflet. The curved portion 1548 may include an extending portion 1549 that is parallel to the protruding portion 1546. The delivery device 1544 may be structured to deliver a repair device when the delivery device surrounds and clamps the leaflet. The protruding portion 1546 may have a shape that corresponds to a repair device. The delivery device may be structured to deliver a repair device, such as repair device 1510 having a connector 1512 that extends from each end of the device, for example, as shown in FIG. 15(*b*). The connector 1512 may be a sharpened metal or alloy, such as a needle. The delivery device may be positioned adjacent to a valve so as to implant or delivery the valve repair device. The delivery device may cause the connector 1554 and 1564 (protruding needle) on each side of the repair device to puncture the leaflet, for example, as shown in FIGS. 15(*c*) and (*d*), respectively; and partially or completely surround the leaflet to complete the implantation, for example, as shown in Figures (e) and (f).

Figure 16:
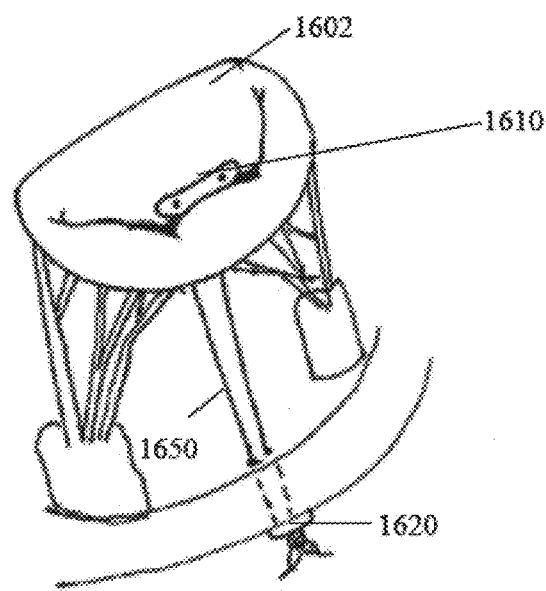
FIG. 16 shows an implanted repair device according to embodiments.

In some embodiments, the repair device may be configured to be attached to a cardiac wall. FIG. 16 shows an example of a repair (implant) device or system 1600 implanted into a valve 1602 according to some embodiments. FIG. 16 shows a system or device 1600 including a valve body 1610 and a port 1620. The repair device 1600 may include also include a mounting structure (not shown). The valve support may preferably be an expandable member such as a balloon. The system may further include connectors (e.g., tubes and/or sutures) 1630 that extend from the openings provided in the valve support 1610 to a port 1620. The port 1620 may be structured to hold the sutures and/or tubing 1630 thus helping to secure the repair device with respect to the leaflets. The port may also be structured to provide access to the valve support. The port may be structured to deliver fluid to the valve support for expanding the valve support, as well as retrieve fluid from the artificial member for deflating the artificial member.

According to some embodiments, the port may remain in the heart after the repair device is implanted so that further adjustments to the valve support may be made. In other embodiments, the port may be removed after the repair device is implanted (and adjusted).

In some embodiments, the systems may deliver the repair device through a catheter. The repair device may be structured to be delivered through the catheter in a closed position through a hole in a leaflet and opened to an open position after either part or full length of the device passes beyond the leaflet. The repair device may have a shape that extends beyond the opening on the leaflet surface. The surface of the repair device may further include sutures and/or tubing that extend from the repair device to the point of access. In some embodiments, the repair device may be fixedly disposed to the leaflet without sutures or any connectors on the leaflet. The repair device may fix the sutures and/or connectors to the port disposed at the point of access.

Figures 17A, 17B:
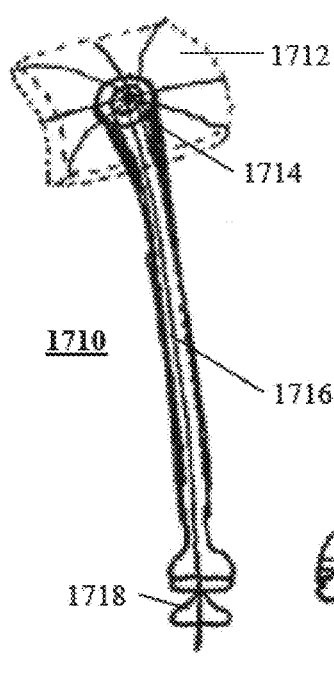
FIGS. 17(a)-(d) show embodiments of a repair device.
Figure 17C:
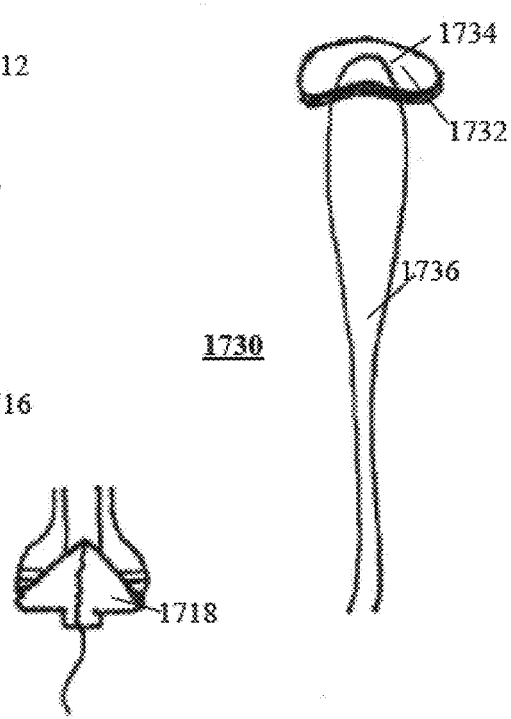
Figure 17D:
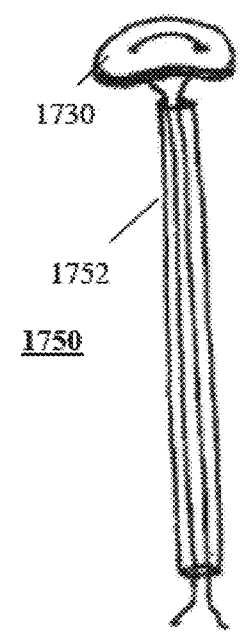

FIGS. 17(*a*)-(*c*) show examples of repair devices and related systems. In some embodiments, for example, as shown in FIGS. 17(*a*) and (*b*), a repair device 1710 may include a valve support 1712 that surrounds a flexible mounting structure 1714. The device 1710 may include a connector (e.g., (tubing) and/or sutures) 1716. The device 1710 may further include a plug 1718 at the end of the sutures/tubing so that when the valve support is in place, the plug may be structured to maintain the position of the repair device (via the port) as shown in FIG. 17(*a*). The repair device 1710 may further be structured to be collapsed so as to be introduced through a delivery lumen and later be expanded after implantation. FIG. 17(*a*) shows an example of a repair device having this structure.

In other embodiments, the repair device may further include a covering member. The covering member may be structured to protect the top surface of the valve support. The covering member may be structured to protect the connecting member such as sutures. The covering member may protect the repair device from invasion and growth of cells. FIGS. 17(*b*) and (*c*) show examples of a repair device including a covering member. FIG. 17(*b*) shows a repair device 1730 according to some embodiments including a covering member 1734 structured to protect a top surface of the valve support 1732 and/or connector site (the suture site) 1733. FIG. 17(*c*) shows a repair system 1750 according to some embodiments including a covering member 1734 structured to protect a top surface of the valve support 1732 and/or the connector site (e.g., opening). The repair device may include a valve support that surrounds a flexible mounting structure and that includes an extending member (tubing).

Figures 18A, 18B, 18C:
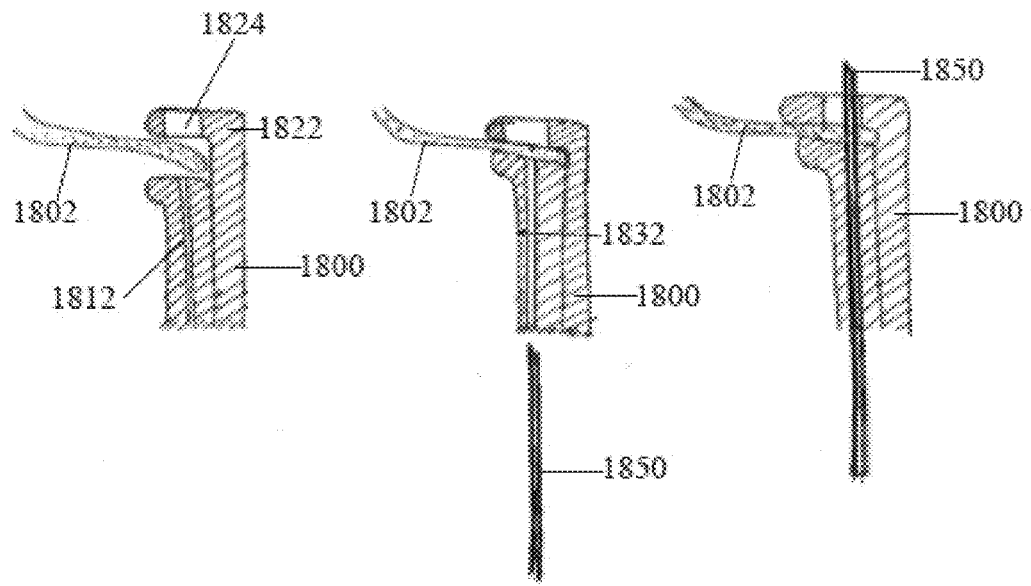
FIGS. 18 (a)-(c) show steps of a method of implanting a repair device with a delivery device according to embodiments.

FIGS. 18 and 19 show a system according to embodiments to implant the repair device, according to some embodiments. The system may include a delivery device, such as a catheter. The delivery device may include two movable sections or members that are structured to clamp an edge of a leaflet. A first movable section or member may include a hollow channel structured to receive a hollow needle. The second movable section or member may include a portion that is parallel to the first movable section and another portion that is perpendicular. The perpendicular portion may include an opening that is above the hollow channel. The length of the perpendicular portion may be based on the position of the opening on the leaflet. The opening may have a larger diameter for the hollow channel.

FIGS. 18(*a*)-(*c*) show the first-third steps of delivering a repair device, respectively. First, a delivery device 1800 may be brought in position with leaflet 1802 so that the leaflet 1802 is provided between a first movable section 1812 and the second movable section 1822 (in an open position). The delivery device 1800 may be positioned so that an edge of the leaflet 1802 abuts the second movable section 1822 (the parallel portion). After the delivery device 1800 is properly positioned, the first and second movable members may be closed so that the leaflet is secured, as shown in FIG. 18(*b*). Then, a hollow needle 1850 may be introduced through a hollow channel 1840 through the leaflet 1802 so as to pierce the leaflet 1802, as shown in FIG. 18(*c*).

Next, as shown in FIGS. 19(*a*) and (*b*), a repair device 1900 may be introduced through the hollow channel 1840. First, in step 4, as shown in FIG. 19(*a*), the repair device 1900 may be delivered past the opening 1824 on the second movable member 1822. Then, in step 5, as shown in FIG. 19(*b*), the second movable member 1822 may be opened to thereby unclamp the leaflet 1802. The opening 1824 of the second movable member 1822 may be structured to the size of the repair device 1900 (in unexpanded state) so that the second movable member 1822 may be capable of moving past the repair device 1900. The repair device 1900 (in unexpanded state) may also alternatively or additionally be flexible so that the second movable member 1822 may be capable of moving past the repair device 1900. The position of the repair device 1900 may then stabilized and secured and thus the repair device may then be expanded.

Then, the valve support of the repair device may be expanded. FIG. 20 shows an example 2000 of a repair device 2010 according to embodiments implanted onto a leaflet 2002. The repair device 2010 may include a valve support 2020 and a mounting structure 2030. The valve support 2020 may be an expandable impermeable member, such as balloon, that surrounds the mounting structure 2030. The device 2000 may include a connector 2040 that is structured to anchor the valve support 2020 to a cardiac wall. The connector 2040 may extend from the mounting structure 2030 to a port 2050. The repair device 2010 may further include hollow tubing 2042 that also extends from the valve support 2020 and surrounds the connector 2040 to the port 2050. The port 2050 may be structured to be disposed on the other side of the heart at the point of access. The port 2050 may include at least one fluid conduit 2054 structured for injections of a fluid like saline into the balloon to cause the balloon to expand.

Figures 21A, 21B:
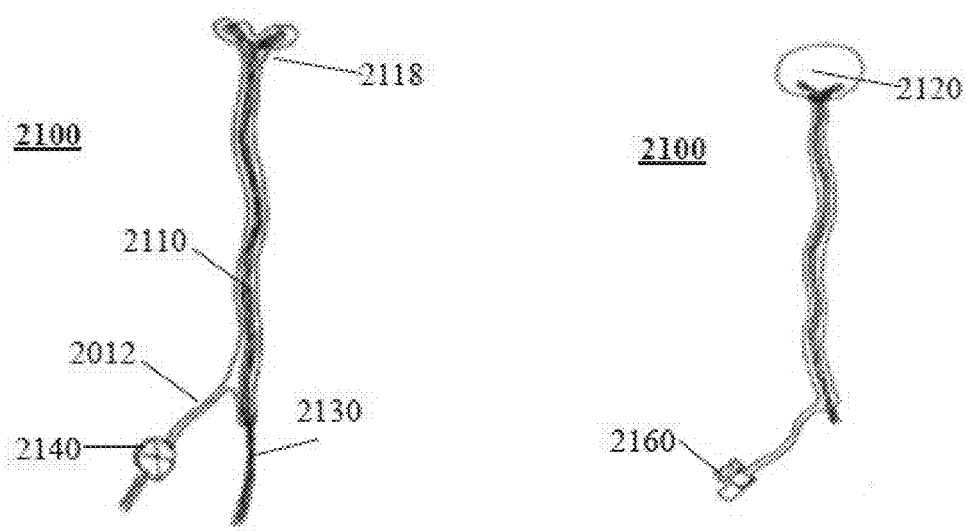
FIGS. 21(a) and (b) show a repair device according to embodiments.

FIGS. 21(*a*) and (*b*) show an example of a repair device 2100 according to these embodiments in an unexpanded state and an expanded (inflated) state, respectively. According to some embodiments, the repair device 2100 may include tubing 2110 and a connector 2130 that separates at a point along the length. In some embodiments, the tubing 2110 may be a double lumen. The outermost lumen 2112 may be structured to deliver the fluid or saline through the valve 2140. An end of the inner lumen 2118 may be integrated with or attached to the structural anchor to secure or fix the repair device to the leaflet. The other end of the inner lumen 2118 may also connect the repair device to the port. The repair device may further include a valve 2140 after the tubing and structural anchor separate. The valve 2140 may be used for fluid injection to expand the valve support 2120. In some embodiments, the valve 2140 may be connected to the port 2150 provided in the access site. In some embodiments, the valve 2140 may be secured to the access site for example, by sutures, and remain in the access site after implantation for further adjustments of the repair device. In other embodiments, the valve 2140 may be removed after the repair device is implanted and adjusted to the desired expansion.

According to some embodiments, the port may include a plurality of fluid conduits. In other embodiments, the port may include one fluid conduit. In further embodiments, for example, as shown in FIG. 22(*a*), a device 2210 may include a port 2212 structured for one repair device 2214 through connector 2220. In other embodiments, the port may be structured to receive more than one repair device. The port may be structured to receive more than one repair device through one access point. Extending members of each repair device may converge into one connector (also referred to as extending member) that connects to an access point on a port. FIG. 22(*b*) shows a system 2230 including two repair devices 2234, 2236 that connect to a port 2232 through one connector 2240. In other embodiments, the port may have a plurality of access points. The port may be structured to receive a repair device through a respective access point. The port may be structured to receive more than one repair device through each respective fluid conduit. FIG. 22(*c*) shows a system 2250 including two repair devices 2256, 2258 that each connect to a port 2270 through access points 2252 and 2254 by connectors 2262 and 2264, respectively.

FIG. 23 shows a repair system 2300 mounted on a leaflet 2302 according to some embodiments. The repair system 2302 may include a valve support 2310 (e.g., a balloon) that has two separate, connectors 2312 and 2322 that individually connect to a port 2340. The connectors 2312 and 2322 may further include tubing or lumens 2340 and 2350, respectively, according to embodiments.

Figure 24:
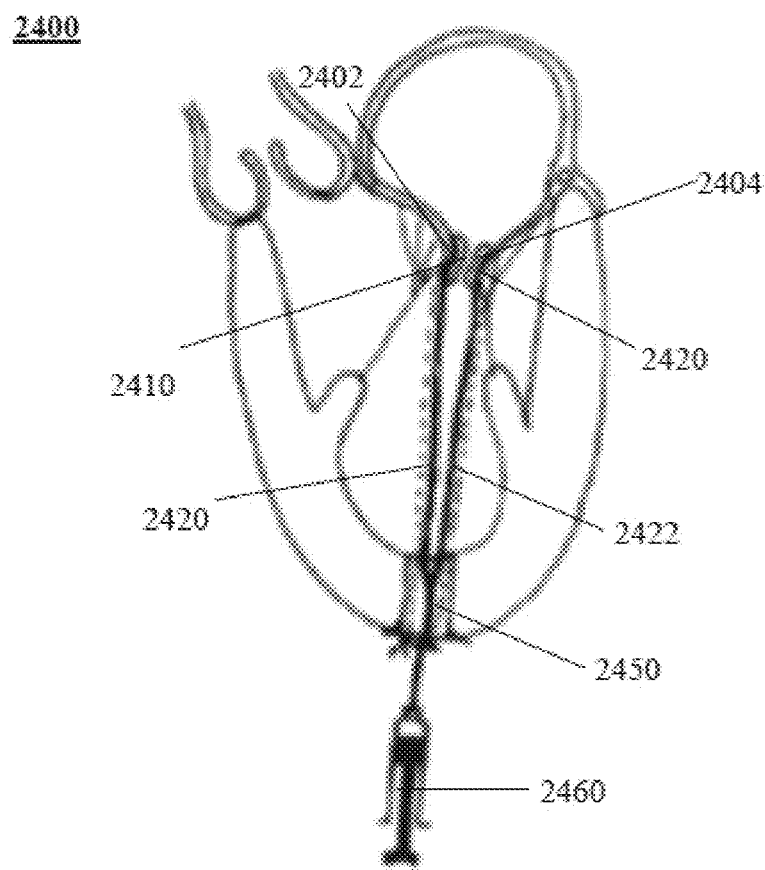
FIG. 24 shows a repair system according to embodiments implanted onto a valve.
Figure 25A:
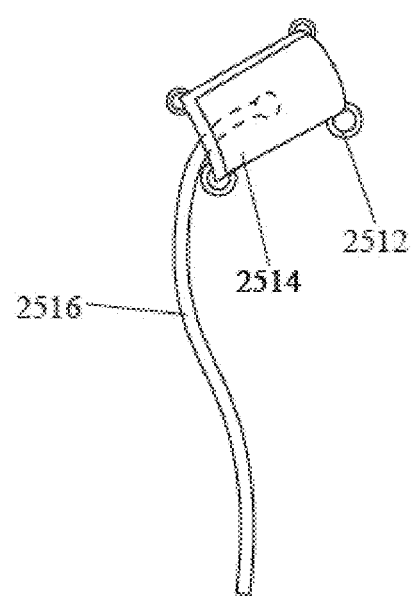
FIGS. 25(a)-(f) show methods of implanting repair devices according to embodiments.
Figure 25B:
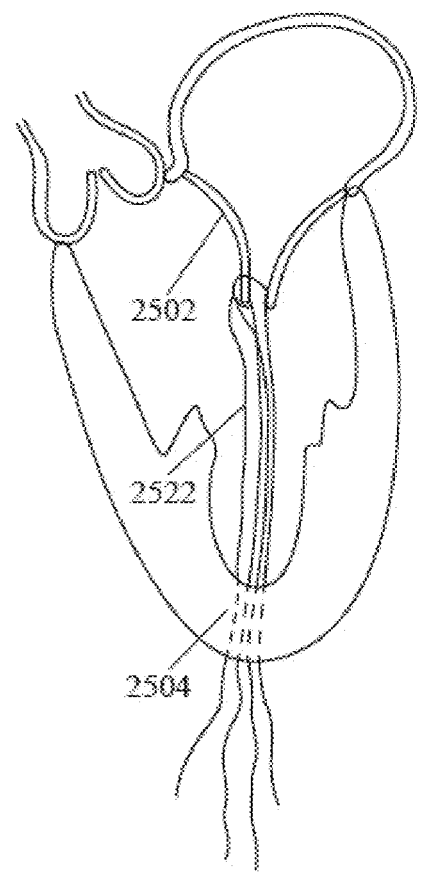
Figure 25C:
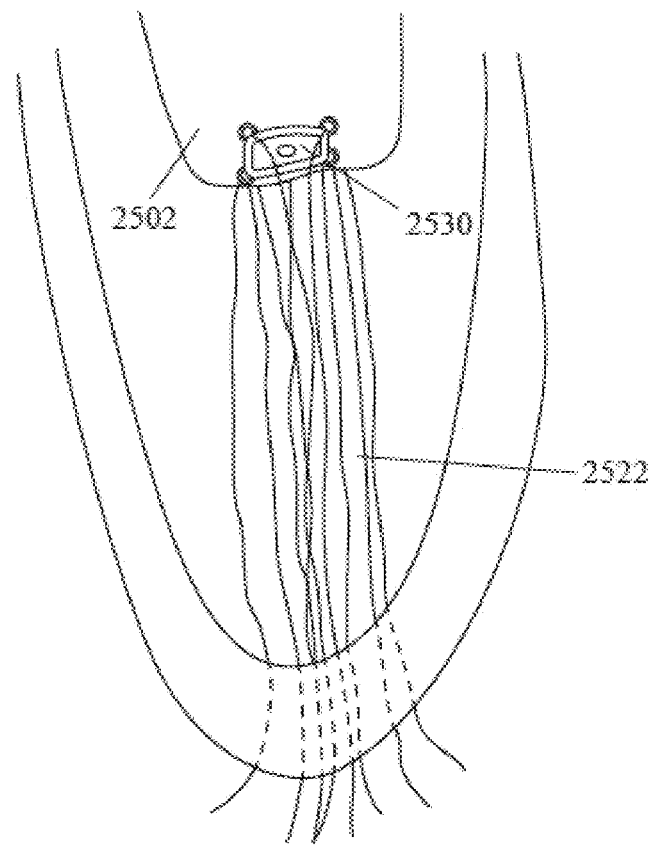
Figure 25D:
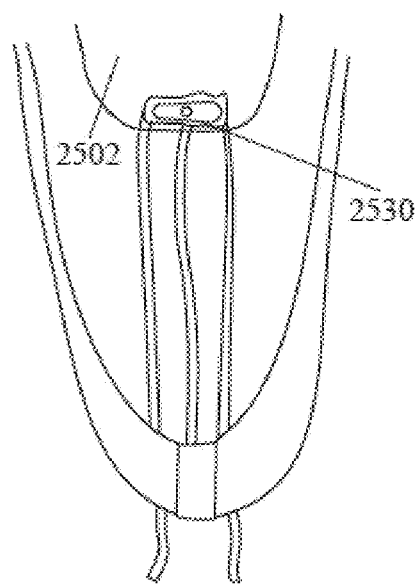
Figure 25E:
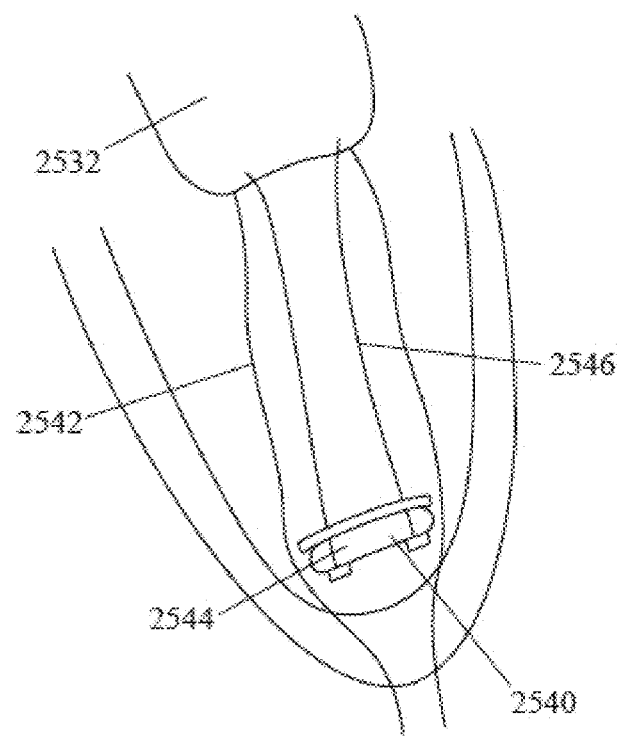
Figure 25F:
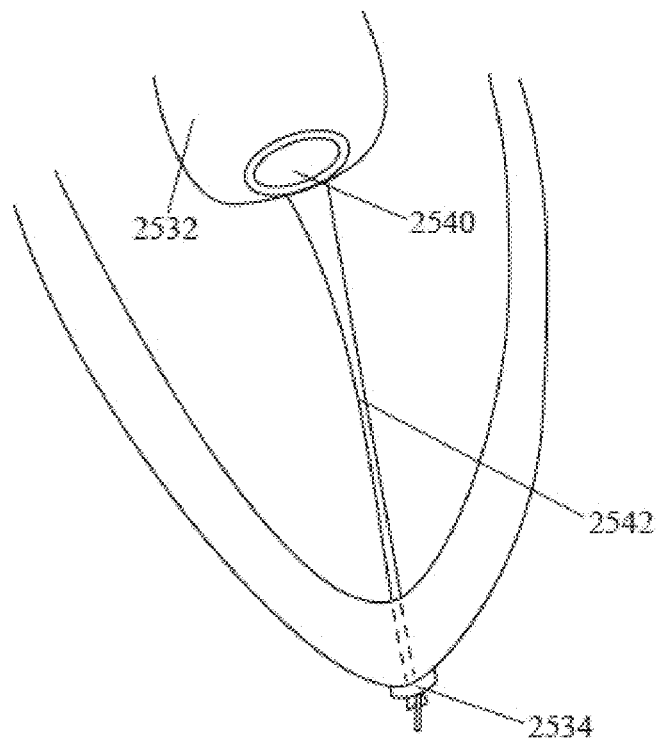

In some embodiments, for example, as shown in FIG. 24, a repair system 2400 may include two repair devices 2410, 2420 that are structured to be implanted onto two opposing leaflets 2402, 2404. The repair system 2400 may include separate tubing and/or connectors 2420, 2422 that may converge into one tubing and/or anchor that connects to a port 2450. In other embodiments, the repair system may include a repair device for each leaflet. FIG. 24 also shows an example of a device 2460 configured to inject fluid through the port 2450 to each repair device 2410, 2420.

FIGS. 25 (*b*) through (*f*) show methods to implant repair devices according to different embodiments. FIG. 25(*b*)-FIG. 25(*d*) show a method of implanting a repair device according to some embodiments, for example, a repair device as shown in FIG. 25(*a*). FIGS. 25(*e*) and (*f*) show a method of implanting a repair device according to other embodiments. However, it will be understood that the methods shown in FIGS. 25(*b*) through (*f*) may be used to implant repair devices according to other embodiments.

In some embodiments, a repair device 2510 may include a valve support 2512, a mounting structure (not shown), a plurality of openings 2514 (e.g., four openings place at each corner) configured for sutures, and optionally include connector 2516 (e.g., a lumen), as shown in FIG. 25(*a*). First, at least one suture 2522 for each opening (or connector site provided on the repair device) may be implanted into a leaflet 2502 through an access point 2504 provided in the cardiac wall (e.g., the apex of the heart), as shown in FIG. 25(*b*). Next, a repair device 2530, such as the repair device 2510, may be positioned on the leaflet using the suture(s) 2522, as shown in FIG. 25(*c*). FIG. 25(*d*) shows the repair device 2530 implanted on the leaflet 2502 after the procedure is completed.

FIGS. 25 (*e*) and (*f*) show a method of implanting a repair device 2540 that may include at least one connector (e.g., two sutures) 2542 that are secured to a valve support 2544 and/or mounting structure 2546 according to embodiments (for example, such as repair devices as shown in FIGS. 9(*d*) and (*i*)). After the sutures 2542 are implanted into a leaflet 2532, for example, as shown in FIG. 25(*b*), the repair device 2540 may be pushed along the sutures until it reaches the leaflet, as shown in FIG. 25(*e*). Then, after the repair device 2540 is properly positioned, the sutures 2542 may be secured at the point of access 2534, as shown in FIG. 25(*f*). The sutures may be secured using a port according to embodiments.

In some embodiments, the repair device may include more than one valve support configured to be disposed on opposing sides of a valve leaflet. FIGS. 26 through 37 show examples of a repair device according to these embodiments. The repair device may incorporate any of the embodiments of the repair device discussed above.

FIG. 26 shows an example of a repair device 2600. The repair device may include a first valve support 2612 configured to be disposed on top or the atrial side or surface of a leaflet and a second valve support 2614 configured to be disposed on the bottom or the ventricular side or surface of a leaflet. The valve supports 2612 and 2614 may be separated by a gap 2620. The device 2600 may further include a mounting structure for each valve support. The device 2600 may include a first mounting structure 2632 configured to be disposed between the valve support 2612 and a leaflet surface and a second mounting structure 2634 configured to be disposed between the valve support 2614 and the opposing leaflet surface. The device 2600 may further include a connector 2640 configured to anchor the valve supports to an access point provided on a cardiac wall.

In some embodiments, the valve implant device may be an impermeable, flexible member configured to be expanded, for example, by a liquid and/or gas. The device 2600 may include at least one lumen configured to receive a liquid and/or gas. The device may include any number of lumens. As shown in FIG. 26, the device 2600 may include two lumens 2644 and 2646. The device 2600 may also include a central lumen 2642 configured for a guidewire. The device 2600 may also include a port 2650 (embodiments described in further detail below).

Figure 27:
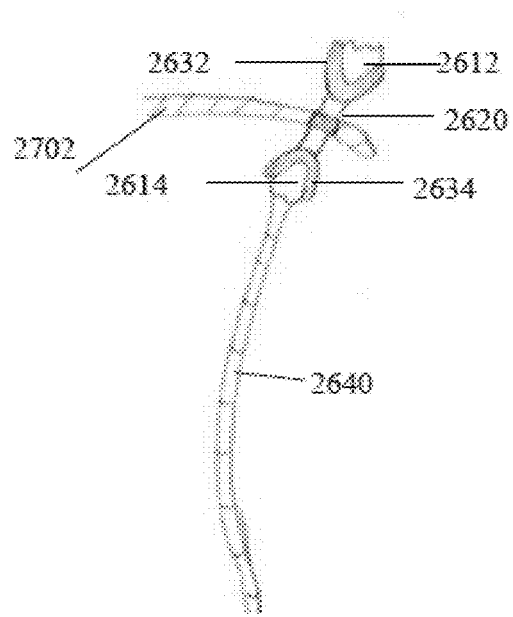
FIG. 27 shows another view of the repair device of FIG. 26.
Figure 28:
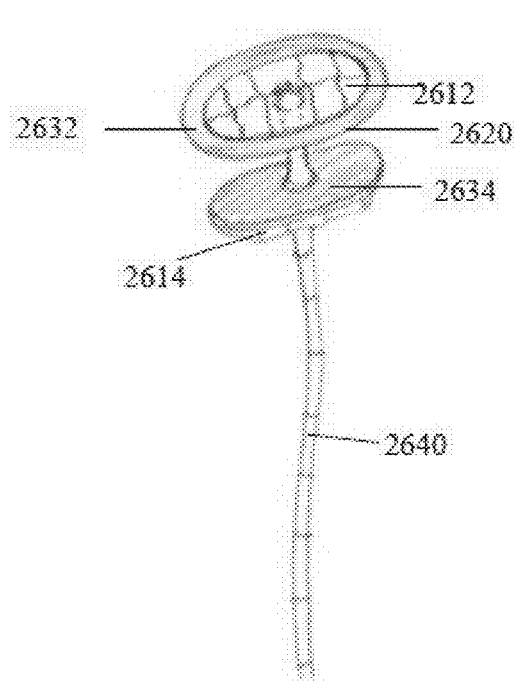
FIG. 28 shows another view of the repair device of FIG. 26.
Figure 29:
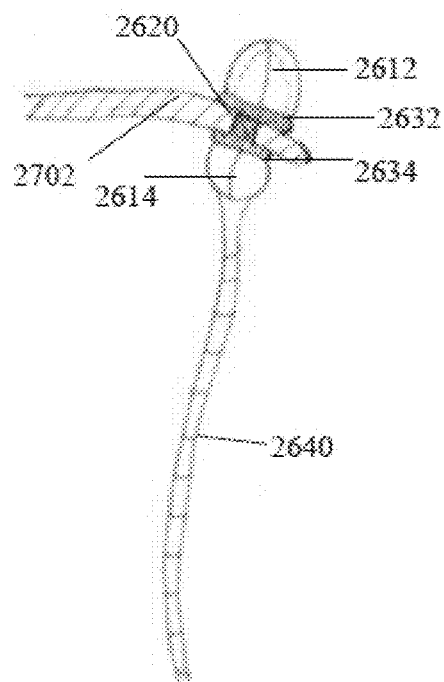
FIG. 29 shows another view of the repair device of FIG. 26.
Figure 30:
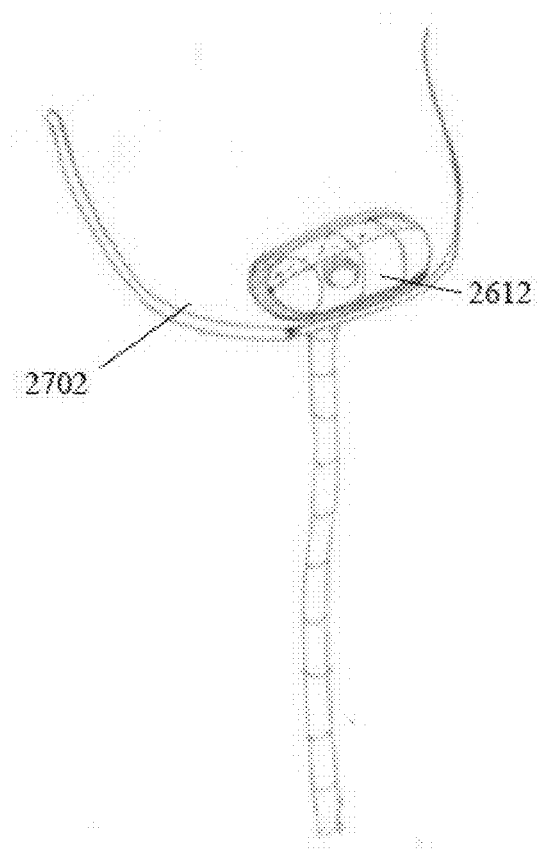
FIG. 30 shows an atrial side of an implanted repair device according to embodiments.
Figure 31:
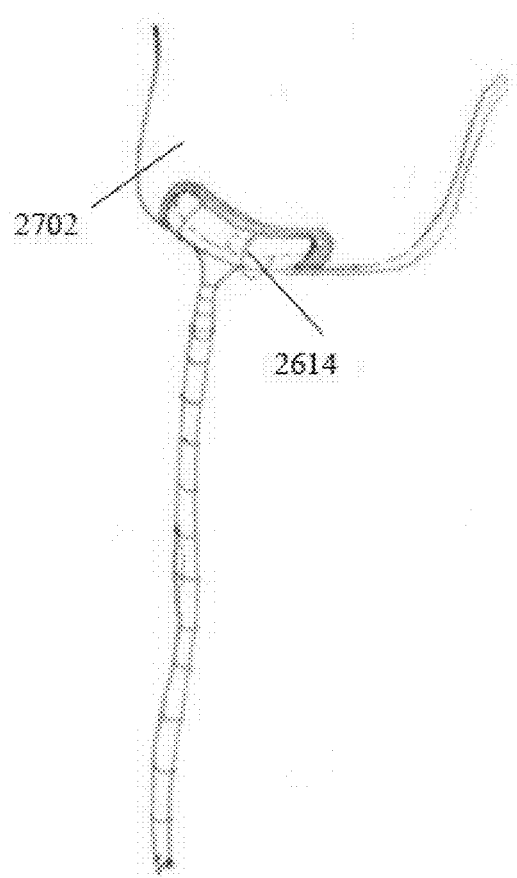
FIG. 31 shows a ventricular side of an implanted repair device according to embodiments.

FIG. 27 shows the device 2600 in an unexpanded state implanted on a leaflet 2702. FIG. 28 shows the device 2600 in an expanded state and FIG. 29 shows a side view of the device 2600 in an expanded state implanted on a leaflet 2702. FIG. 30 shows a top/atrial view of the device 2600 implanted on a valve 2702 and FIG. 31 shows a bottom/ventricular view of the device 2600 implanted on a valve 2702.

The repair device 2600 may be configured to expand the valve supports sequentially, simultaneously, or some combination thereof. In some embodiments, the atrial valve support (support 2612) may be configured to be expanded before the ventricular valve support (support 2614) may be expanded. FIG. 35 shows an example of the repair device 2600 being filled with a liquid 3502, such as a saline solution. As shown in FIG. 35, the repair device 2600 may be configured so that the first valve support 2612 may be expanded before the second valve support 2614 may be expanded.

Figure 36:
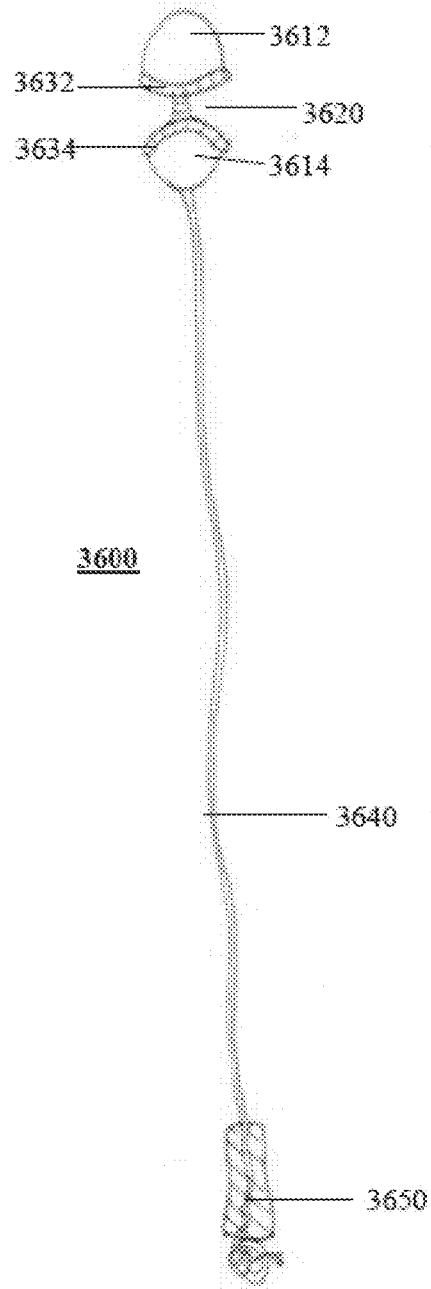
FIG. 36 shows a repair device according to embodiments.

In other embodiments, the valve support(s) may be made of a self-expanding material, such as a hydrophilic material, that is configured to expand when exposed to blood. FIG. 36 shows an example of a device according to these embodiments. As shown in FIG. 36, a repair device 3600 may include first and second valve supports 3612 made of a hydrophilic material, mounting structures 3632 and 3634, and a gap 3620 there between. The mounting structures 3632 and 3634 may be made of a memory shape alloy, such as Nitinol, that is configured to expand with the valve supports. In some embodiments, the device 3600 may include a connector 3640, such as a suture or other fastener, configured to connect the device to a port 2650 configured to be implanted at an access point along a cardiac wall, such as the ventricular apex.

Figure 32:
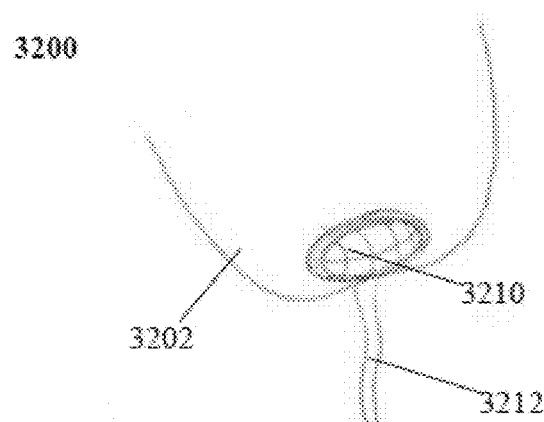
FIG. 32 shows a repair device according to embodiments.
Figure 33:
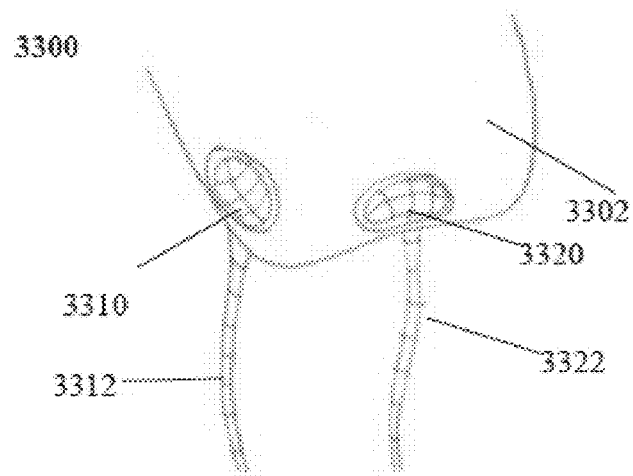
FIG. 33 shows a repair device according to embodiments.
Figure 34:
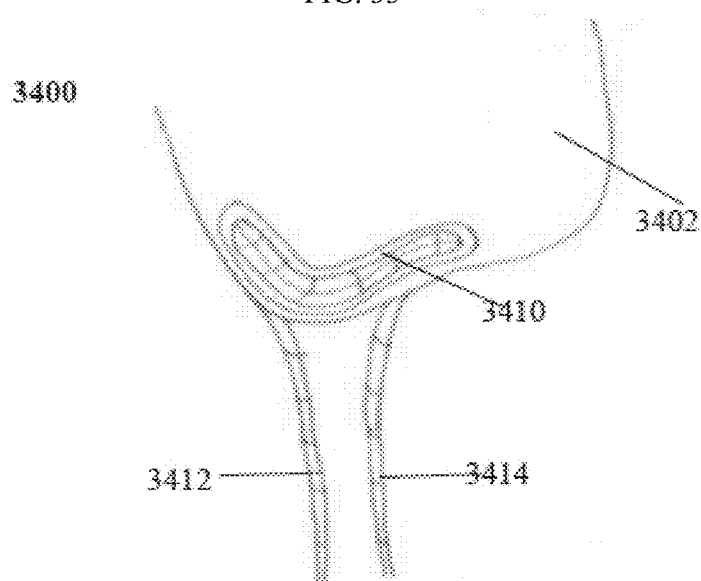
FIG. 34 shows a repair device according to embodiments.

FIGS. 32 through 34 show examples of a repair device. In some embodiments, one repair device 3210 may be implanted on a leaflet 3202, as shown in FIG. 32. Like the repair device shown in FIG. 22(*a*), the repair device according to embodiments is not limited to that configuration and may have different configurations. There may be more than one repair device implanted onto a leaflet, more than one connector, or some combination thereof. In other embodiments, repair devices 3310 and 3320 may be implanted on a leaflet 3302, as shown in FIG. 33. Each repair device 3310 and 3320 may each include a connector 3312 and 3322, respectively. In certain embodiments, a repair device 3410 implanted on a leaflet 3402 may include more than one connector (connectors 3412 and 3414), as shown in FIG. 34.

Figure 37A:
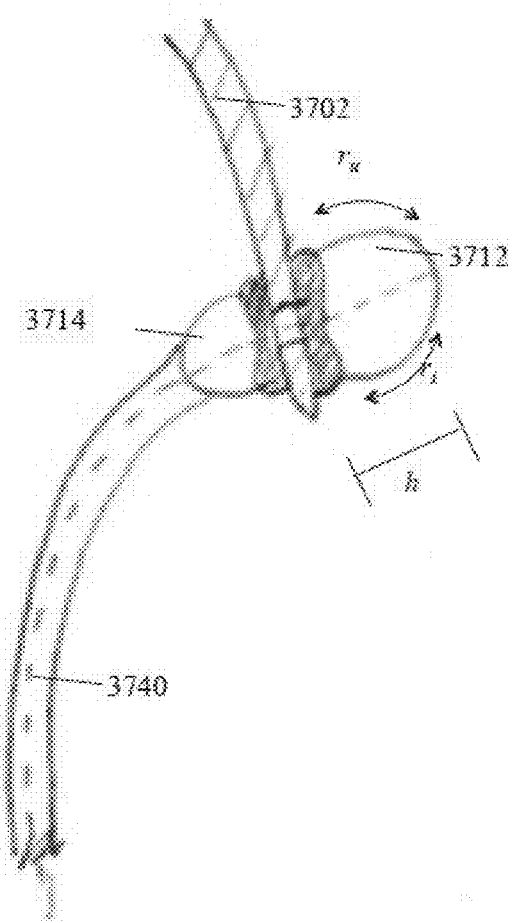
FIGS. 37(a) and (b) show partial side and top views of a repair device according to embodiments.
Figure 37B:
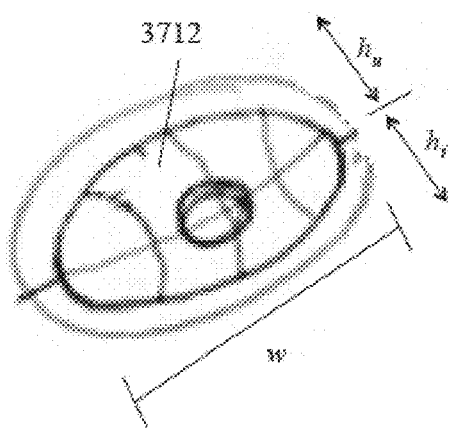

In some embodiments, the valve supports may have the same shape, different shape, or some combination thereof in an expanded state. In some embodiments, the dimensions (e.g., radius, height (h), width (w), length) of each valve support may vary. For example, as shown in FIGS. 37(*a*) and (*b*), the device 3700 shown implanted on a leaflet 3702 may include a valve structure 3712 that is larger than the valve structure 3714. In some embodiments, the radius ($r_u$) on one side may be different (less and/or more) or the same as the radius ($r_l$) on the other side. In some embodiments, the height ($h_u$) on one side may be different (less and/or more) or the same as the height ($h_l$) on the other side. In some embodiments, the dimensions of the valve support may depend on valve anatomy.

In some embodiments, the repair devices and systems may include a port system configured to expand and anchor the repair device. FIGS. 38-41 show examples of a port system according to embodiments.

Figure 38:
FIG. 38 shows a partial view of a port system of a repair device according to embodiments.

As shown in FIG. 38, system 3800 include an adapter 3900 disposed at an end of a connector 3820 and a port 4000 (also referred to as "ventricular port") configured to be disposed in a cardiac wall, such as the ventricular apex.

Figure 39A:
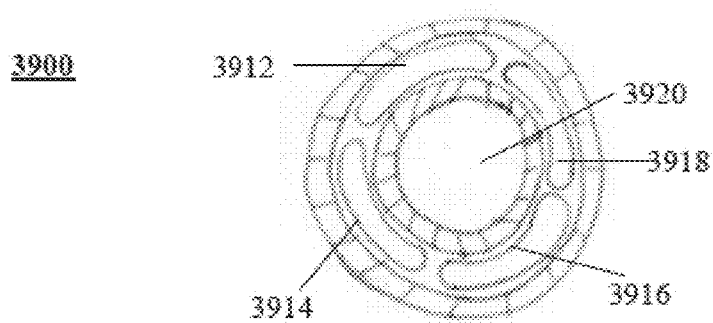
FIGS. 39(a) and (b) show a bottom view and a partial cross-sectional view of an adapter according to embodiments.
Figure 39B:
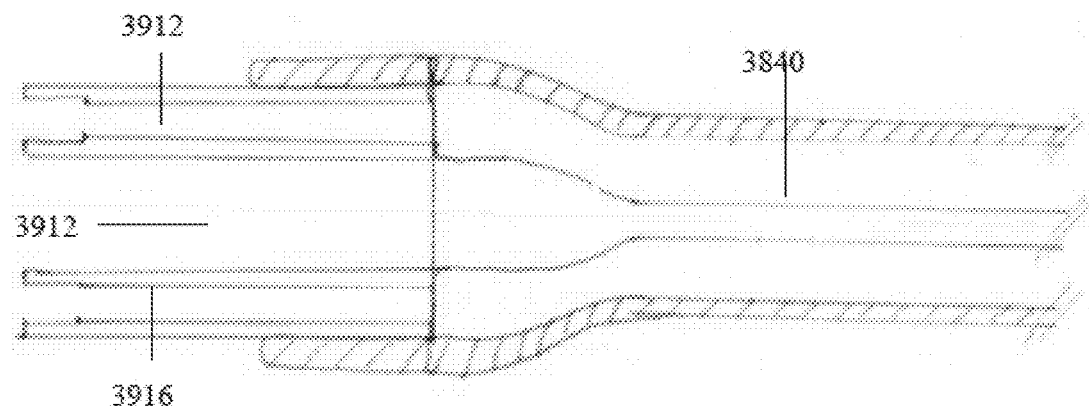

As shown in FIGS. 39(*a*) and (*b*), the adapter 3900 may include at least one lumen configured to deliver a liquid/gas to expand a valve support. The adapter 3900 may include four lumens 3912, 3914, 3916, and 3918. The port 3900 may include more or less lumens. The lumens may surround a central lumen 3920 configured to receive a guidewire and/or introducer.

Figure 40A:
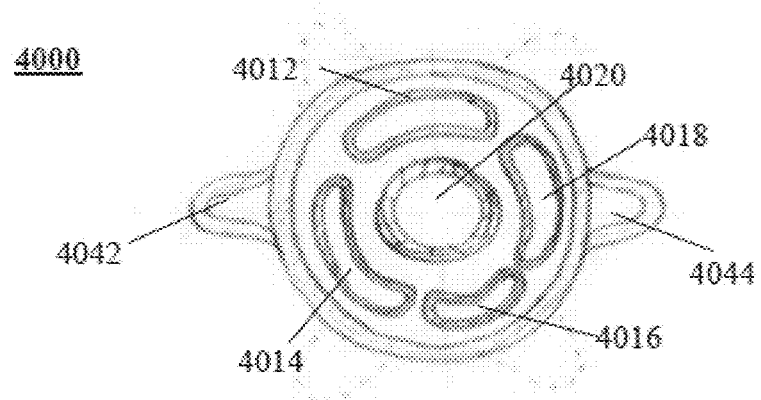
FIGS. 40 (a)-(c) show a top view, a partial cross-sectional view, and a bottom view of a port according to embodiments.
Figure 40B:
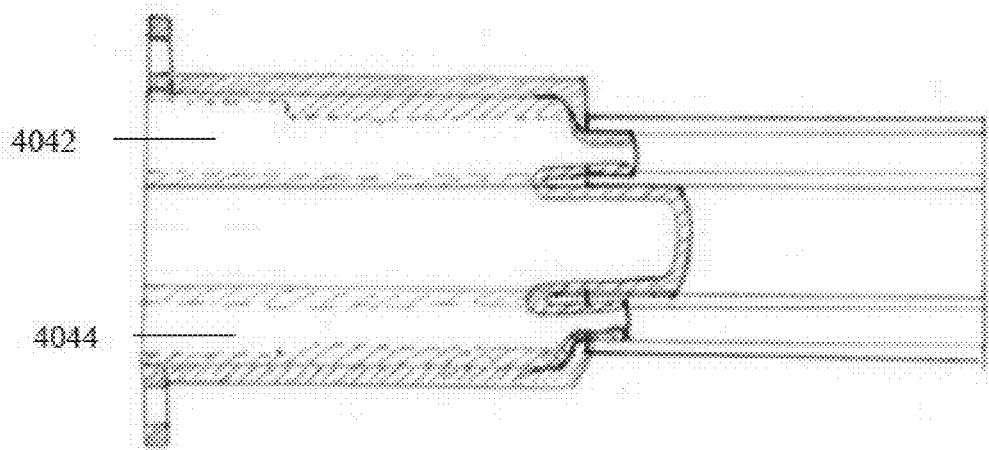
Figure 40C:
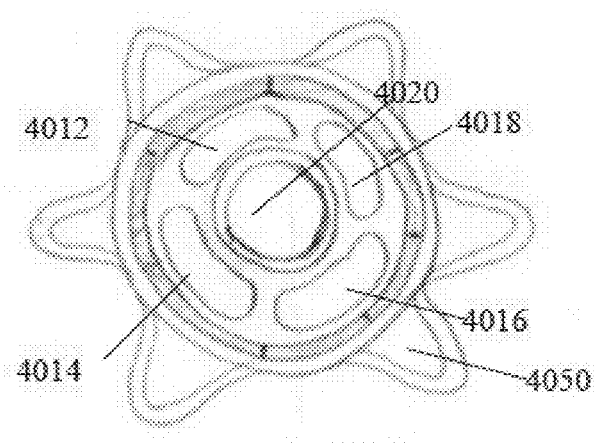

FIGS. 40(*a*)-(*c*) show different views of the port 4000. In some embodiments, the port 4000 may include lumens that are configured to align with the lumens of the adapter 3900. The port 4000 may include the same number and/or size lumens, or may include a different number and size lumens. As shown in FIGS. 40(*b*) and (*c*), the port 4000 may include four lumens 4012, 4014, 4016, and 4018 configured to receive liquid/gas, and a central lumen 4020 configured for a guidewire and/or introducer. The lumens 4012, 4014, 4016, 4018, and 4020 may be configured to be aligned with lumens 3912, 3914, 3916, 3918, and 3920.

In some embodiments, the port 4000 may include a means to implant the port into an access point along the cardiac wall, such as the apex of the heart. The port 4000 may include a plurality of openings 4050 configured for sutures or other fasteners.

In some embodiments, the port 4000 may further include at least one reservoir for storing the gas/liquid to be delivered to a valve support. The reservoir may be configured to store, for example, saline solution, and allow the solution to be mixed with blood to prevent coagulation. As shown in FIGS. 40(*b*) and (*c*), the port 4000 may include reservoirs 4042 and 4044.

In some embodiments, the port 4000 may be configured to be movable with respect to adapter 3900 so that the lumens configured to deliver liquid/gas to the valve supports (s) are no longer aligned, for example, when the valve support(s) have been expanded. In some embodiments, the port 4000 may be configured to be movable with respect to the port 3900 before and/or after the port 4000 is sutured to the cardiac wall.

Figure 41:
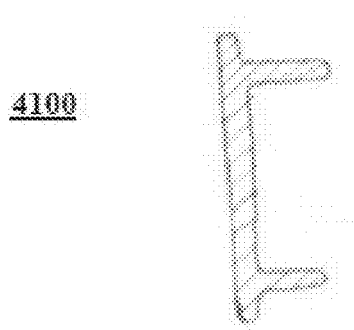
FIG. 41 shows an adapter according to embodiments.

FIG. 41 shows a hub 4100 configured to cover the port 4000 when the procedure is completed. The hub may be structured to be removed so that the port may be re-accessed in the future, for example, for adjustments to the valve support(s).

In some embodiments, the repair system may include and/or be used with a delivery device. In some embodiments, the delivery device may be configured to grasp a leaflet and to allow an introducer that includes a repair device to penetrate the leaflet and move within the delivery device. The delivery device may also be configured to allow the repair device to move past the delivery device.

Figure 42A:
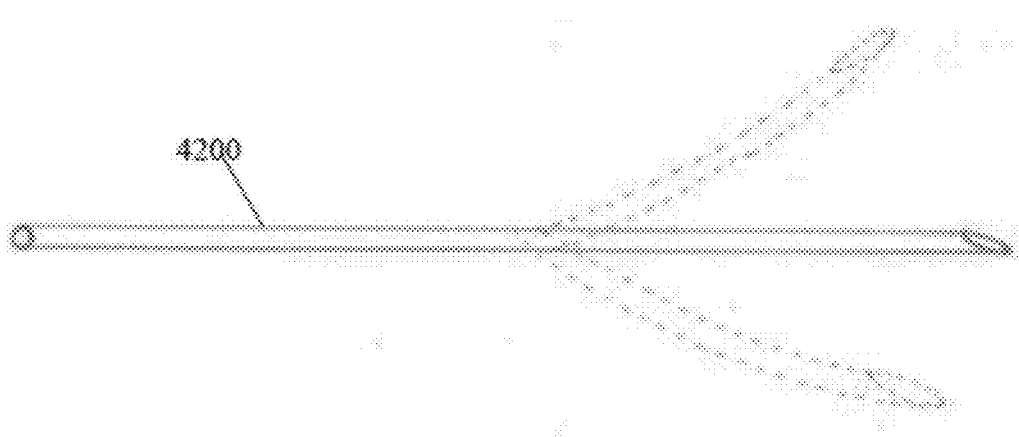
FIGS. 42(a) and (b) show an introducer according to embodiments.
Figure 42B:
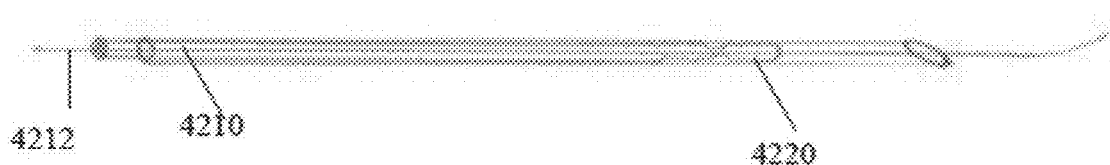

In some embodiments, the repair device may be configured to be disposed within an introducer (in an expanded state). FIGS. 42(a) and (b) show examples of an introducer 4210 and the introducer 4210 in which a repair device 4220 according to embodiments and a guidewire 4212 may be disposed, respectively. In some embodiments, the introducer may be flexible and made of a biocompatible flexible material such as an elastomer or plastic material.

Figure 43A:
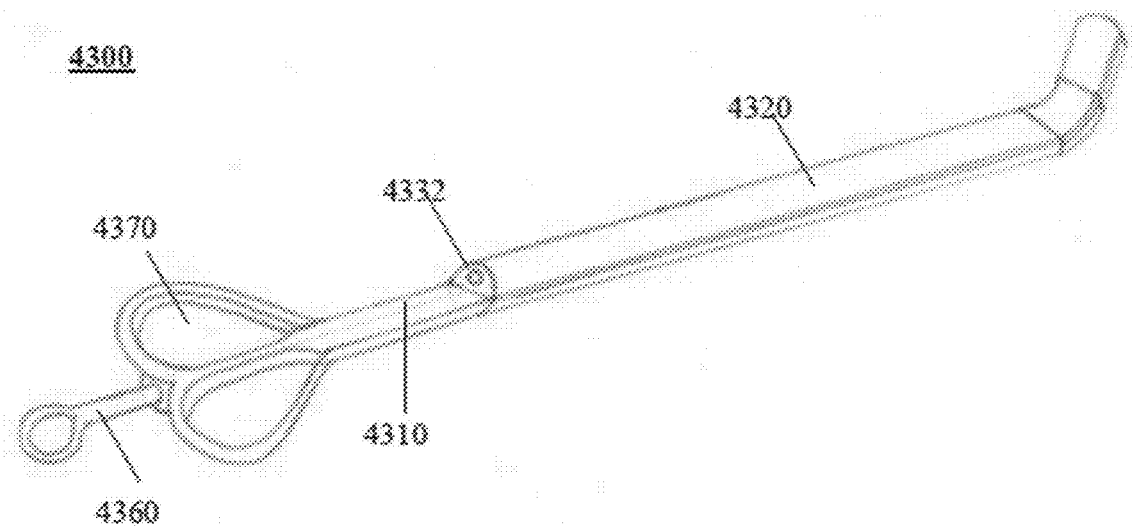
FIGS. 43(a) and (b) show a delivery device according to embodiments.
Figure 43B:
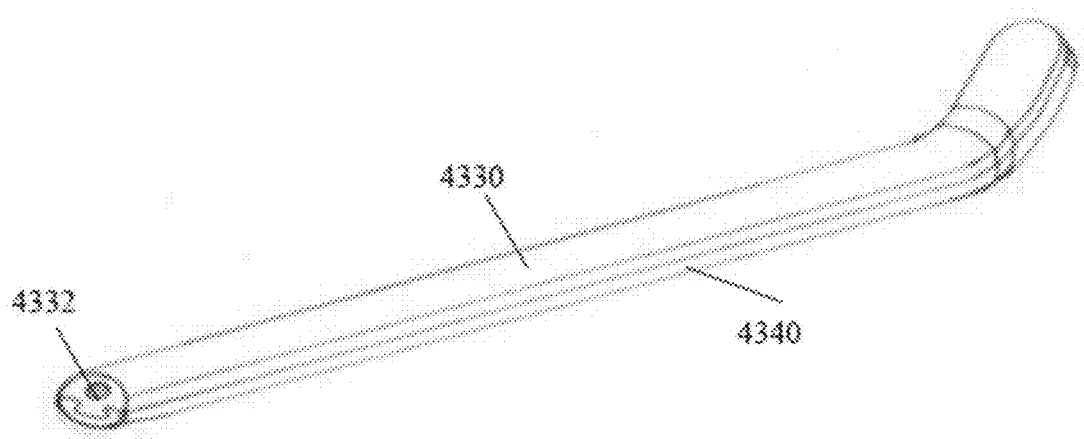
Figure 44A:
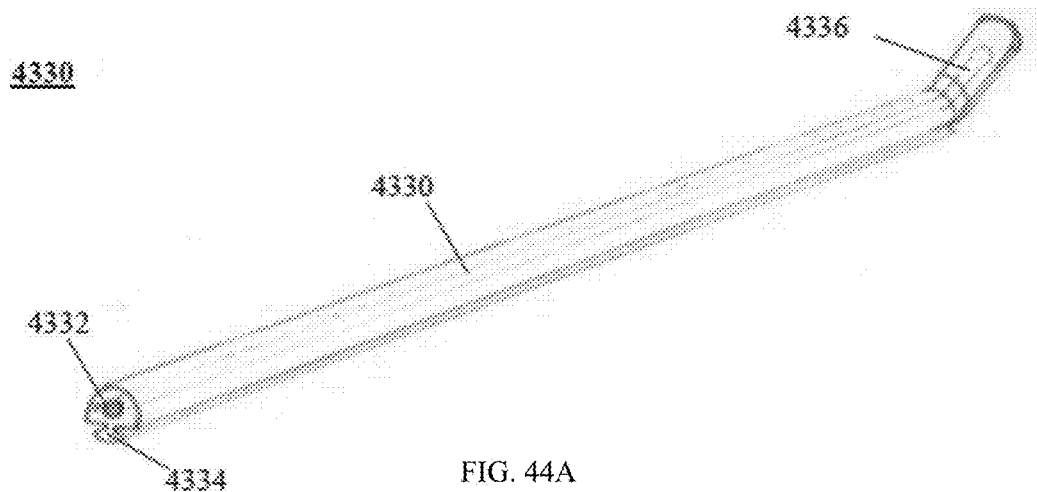
FIGS. 44(a)-(d) show partial, enlarged views of the delivery device of FIGS. 43(a) and (b)
Figure 44B:
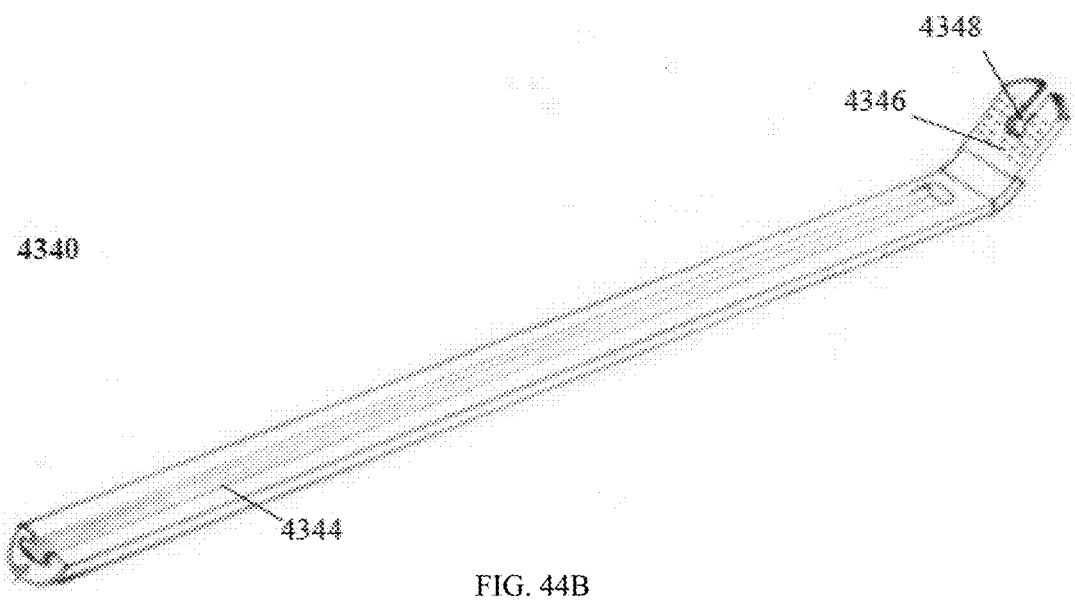
Figure 44C:
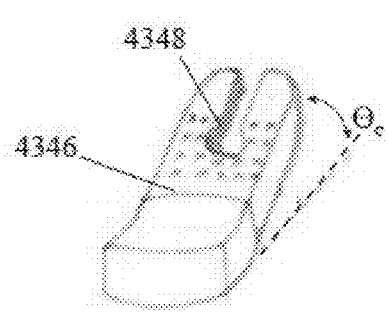
Figure 44D:
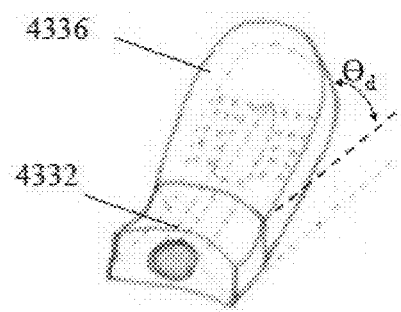
Figure 45A:
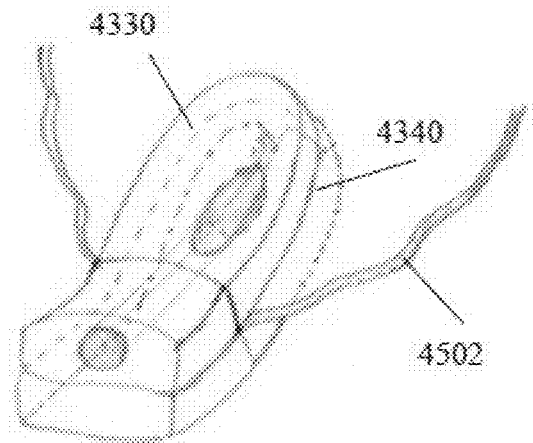
FIGS. 45(a) and (b) show partial orthogonal and side views of the delivery device of FIGS. 43(a) and (b) grasping a leaflet.
Figure 45B:
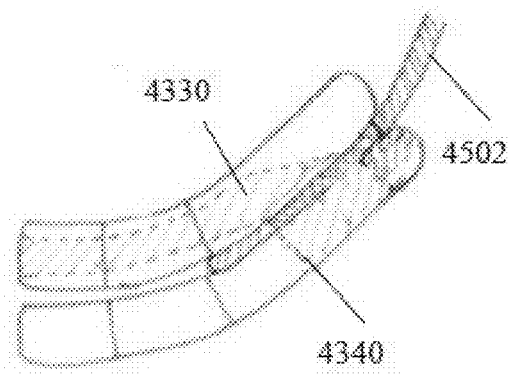

FIGS. 43-45 show examples of a delivery device 4300 according to embodiments. As shown in FIG. 43, the delivery device 4300 may include a handle 4370 configured to maneuver the delivery device, a grasping member 4320, and a plunger 4360. The grasping member 4320 may include more than one segment. The grasping member 4320 may include a first segment 4330 configured to be disposed on the bottom or ventricular side of a leaflet and a second segment 4340 configured to be dispose don the top or atrial side of a leaflet. The plunger 4360 may be configured to move the second segment 4340 with respect to a leaflet.

In some embodiments, the first segment 4330 may include an opening 4332 configured to receive an introducer and/or repair device according to embodiments. The opening 4332 may extend along most of the length to the top of the segment (end 4336). The first segment 4330 may include a fastener 4334 disposed along its length and configured to movably fasten the second segment 4340 with respect to the first segment 4330. The fastener 4334 may be a protruding member. In other embodiments, the fastener 4334 may be a recessed member.

The second segment 4340 may include a fastener 4344 that is complimentary to the fastener 4334. In some embodiments, the fastener 4344 may be a recessed member disposed along its length. In other embodiments, the fastener 4344 may be a protruding member. The second segment 4340 may further include an opening 4348 disposed at end 4346. The opening 4348 may be configured to allow a repair device to be pushed through the opening. The opening 4348 may include more than one portion. In some embodiments, the opening 4348 may include a circular portion and a channel portion.

In some embodiments, the ends 4336 and 4346 may be angled with respect to the axis of the delivery device. The angles θd and c, respectively, may be any angle. The angles θd and c, respectively, may be substantially the same or different. The angle may be configured to allow capture of a leaflet when accessing them, for example, from the ventricular apex.

FIGS. 45(a) and (b) show an orthogonal view and a side view of the delivery device 4300 grasping a leaflet 4502.

According to some embodiments, the systems and repair devices may be single use or be disposable. The system may be further be sterilized. According to some embodiments, a portion or any combination of the repair devices and systems may be sold as a kit.

In some embodiments, the kit may include at least one mounting structure and valve support. In some embodiments, the kit may include a plurality of different valve supports. The valve supports may differ in shape and size. The valve supports may be of the same type or different types (such as a balloon or permeable membrane). In other embodiments, the kit may further include a plurality of mounting structures. The mounting structures may differ in shape and size.

In other embodiments, the kit may include tubing structured to connect the artificial tubing to a port. The kit may include a structural anchor.

In some embodiments, the kit may include sutures. In other embodiments, the kit may include a port.

While various embodiments of the disclosure have been described, the description is intended to be exemplary rather than limiting and it will be appeared to those of ordinary skill in the art that may more embodiments and implementations are possible that are within the scope of the disclosure.

What is claimed:

1. A device structured to be implanted to repair a valve, comprising:
a plurality of valve supports structured to expand;
at least one receiving member extending from the valve supports to a port, the at least one receiving member being structured to expand the valve supports; and
at least one mounting structure structured to be disposed on a surface of a leaflet,
wherein at least one of the valve supports is disposed on the at least one mounting structure.

2. The device according to claim 1, wherein:
the plurality of supports are structured to expand when filled with fluid and/or gas;
the at least one receiving member is structured to receive and deliver the fluid and/or gas to the valve supports; and
the valve supports includes a balloon and/or a permeable membrane.

3. A device for repairing a valve, comprising:
a plurality of valve supports that are structured to expand, the valve supports including a first valve support that is structured to be disposed on an atrial surface of a leaflet of a valve and a second valve support that is structured to be disposed on a ventricular surface of the leaflet; and
at least one connector that extends from the valve supports to a port and is structured to expand the valve supports,
wherein the at least one connector includes two lumens.

4. The device according to claim 3, wherein:
the valve supports are structured to expand when filled with a fluid and/or a gas;
the at least one connector is structured to deliver the fluid and/or the gas to the valve supports; and
the port is structured to be inserted at a ventricular apex.

5. The device according to claim 4, wherein:
the at least one connector includes a hollow tube that extends from the valve supports to a port and is structured to deliver the fluid and/or the gas to expand the valve supports; and
the hollow tube includes a valve structured for an injection of the fluid and/or the gas.

6. The device according to claim 3, wherein at least one of the valve supports is structured to provide a coaptation surface for a valve leaflet.

7. A device for repairing a valve, comprising:
at least two opposing mounting structures, the at least two opposing mounting structures including a first mounting structure and a second mounting structure separated by a gap;
a plurality of valve supports structured to expand, the plurality of valve supports including a first valve support disposed on a surface of the first mounting structure and a second valve support mounted on a surface of the second mounting structure; and at least one connector extending from the valve supports and configured to expand each of the valve supports.

8. The device according to claim 7, further comprising: a port configured to be disposed in a cardiac access point, wherein the at least one connector is configured to connect to the port to anchor the valve supports with respect to the cardiac access point.

9. The device according to claim 1, wherein the device includes two receiving members extending from the valve supports.

10. The device according to claim 1, wherein the valve supports includes a first valve support structured to be disposed on an atrial surface of a leaflet of a valve, and a second valve support structured to be disposed on a ventricular surface of the leaflet.

11. The device according to claim 10, wherein the first valve support and the second valve support are separated by a gap.

12. The device according to claim 1, wherein the at least one receiving member is integrated with the supports.

13. The device according to claim 3, wherein the device includes two connectors, each connector extends from the valve supports to the port and is structured to expand the valve supports.

14. A device for repairing a valve, comprising:
at least one mounting structure structured to be disposed on a surface of a leaflet;
a plurality of valve supports disposed on the at least one mounting structure and structured to expand;
a port configured to be disposed at a cardiac access point; and
at least one connector that extends from the valve supports to the port and is structured to expand the at least one valve support.

15. The device according to claim 14, wherein the port is structured to be inserted at a ventricular apex.

16. The device according to claim 14, wherein:
the at least one connector includes a hollow tube that extends from the at least one valve support to a port and is structured to deliver a fluid and/or a gas to expand the at least one valve support; and
the hollow tube includes a valve structured for an injection of the fluid and/or the gas.

17. The device according to claim 14, wherein the device includes two connectors, each connector extending from the valve supports to the port and is structured to expand the at least one valve support.

18. The device according to claim 14, wherein the device includes a first valve support that is structured to be disposed on an atrial surface of a leaflet of a valve, and a second valve support that is structured to be disposed on a ventricular surface of the leaflet.

19. The device according to claim 14, wherein each mounting structure has an elongated shape.

* * * * *